United States Patent
Baek

(10) Patent No.: US 12,390,444 B2
(45) Date of Patent: Aug. 19, 2025

(54) STABILIZING VITAMIN C TOPICAL FORMULATIONS

(71) Applicant: MF Beauty Partners LLC, Irving, TX (US)

(72) Inventor: Jihoon P. Baek, Los Angeles, CA (US)

(73) Assignee: MF Beauty Partners LLC, Irving, TX (US)

(*) Notice: Subject to any disclaimer, the term of this patent is extended or adjusted under 35 U.S.C. 154(b) by 0 days.

(21) Appl. No.: 17/965,633

(22) Filed: Oct. 13, 2022

(65) Prior Publication Data

US 2023/0057927 A1    Feb. 23, 2023

Related U.S. Application Data

(63) Continuation of application No. PCT/US2021/027830, filed on Apr. 16, 2021.

(60) Provisional application No. 63/010,878, filed on Apr. 16, 2020.

(51) Int. Cl.
| | | |
|---|---|---|
| *A61K 31/375* | (2006.01) | |
| *A61K 8/34* | (2006.01) | |
| *A61K 8/365* | (2006.01) | |
| *A61K 8/67* | (2006.01) | |
| *A61K 9/00* | (2006.01) | |
| *A61K 31/17* | (2006.01) | |
| *A61K 31/19* | (2006.01) | |

(52) U.S. Cl.
CPC ............ *A61K 31/375* (2013.01); *A61K 8/345* (2013.01); *A61K 8/365* (2013.01); *A61K 8/676* (2013.01); *A61K 9/0014* (2013.01); *A61K 31/17* (2013.01); *A61K 31/19* (2013.01)

(58) Field of Classification Search
CPC .... A61K 31/375; A61K 9/0014; A61K 8/676; A61K 31/17; A61K 8/345; A61K 8/365; A61K 31/19

See application file for complete search history.

(56) References Cited

U.S. PATENT DOCUMENTS

| | | |
|---|---|---|
| 2,539,483 A | 1/1951 | Ruskin |
| 4,960,764 A | 10/1990 | Figueroa et al. |
| 4,983,382 A | 1/1991 | Wilmott et al. |
| 5,140,043 A | 8/1992 | Darr et al. |
| 5,308,621 A | 5/1994 | Taylor et al. |
| 5,670,139 A | 9/1997 | Allard et al. |
| 5,736,567 A | 4/1998 | Cantin et al. |
| 5,801,192 A | 9/1998 | Dumas et al. |
| 5,925,679 A | 7/1999 | Mather et al. |
| 6,013,255 A | 1/2000 | Edens et al. |
| 6,020,367 A | 2/2000 | Duffy et al. |
| 6,146,664 A | 11/2000 | Siddiqui |
| 6,361,783 B2 | 3/2002 | Moaddel et al. |
| 6,462,025 B2 | 10/2002 | Vishnupad |
| 7,108,860 B2 | 9/2006 | Dueva et al. |
| 7,179,841 B2 | 2/2007 | Zielinski et al. |
| 8,313,756 B1 | 11/2012 | Landau et al. |
| 8,344,024 B2 | 1/2013 | Czarnota et al. |
| 9,018,177 B2 | 4/2015 | Lauten et al. |
| 9,132,080 B2 | 9/2015 | Zecchino et al. |
| 9,248,082 B2 | 2/2016 | Pinnell et al. |
| 9,901,533 B2 | 2/2018 | Zecchino et al. |
| 10,149,808 B2 | 12/2018 | Pan et al. |
| 10,435,536 B2 | 10/2019 | Swanzy |
| 10,532,017 B2 | 1/2020 | Lema et al. |
| 2001/0007653 A1 | 7/2001 | Moaddel et al. |
| 2004/0033963 A1 | 2/2004 | Yu et al. |
| 2004/0067890 A1 | 4/2004 | Gupta |
| 2004/0219122 A1 | 11/2004 | Masuda et al. |
| 2005/0008592 A1 | 1/2005 | Gardel et al. |
| 2005/0154054 A1 | 7/2005 | Zielinski et al. |
| 2007/0003536 A1 | 1/2007 | Zimmerman et al. |
| 2007/0077261 A1 | 4/2007 | Zhang |
| 2007/0172436 A1 | 7/2007 | Zhang |
| 2008/0057014 A1 | 3/2008 | Masuda et al. |
| 2008/0175919 A1 | 7/2008 | Mohammadi et al. |
| 2008/0274068 A1 | 11/2008 | Tanaka et al. |

(Continued)

FOREIGN PATENT DOCUMENTS

| | | |
|---|---|---|
| CN | 1192134 A | 9/1998 |
| CN | 101282708 A | 10/2008 |

(Continued)

OTHER PUBLICATIONS

Hu et al., CN 110368326, published: Oct. 2019, English machine translation obtained May 6, 2023. (Year: 2023).*

Belcher, L. A. et al. "Evaluating 1,3-Propanediol for Potential Skin Effects." Cosmetics & Toiletries, vol. 125, No. 5, May 2010, pp. 1-4.

Choi, Y.K. et al., "Effects of vitamin C vs. multivitamin on melanogenesis: comparative study in vitro and in vivo," International journal of Dermatology, vol. 49, Iss. 2, Feb. 2010, pp. 218-226.

Espinal-Perez, L.E. et al., "A double-blind randomized trial of 5% ascorbic acid vs. 4% hydroquinone in melasma," International Journal of Dermatology 43(8), Aug. 2004, pp. 604-607.

European Patent Office, Extended European Search Report, European Patent Application No. 19874453.4, Jun. 27, 2022, nine pages.

(Continued)

*Primary Examiner* — Genevieve S Alley

(74) *Attorney, Agent, or Firm* — Fenwick & West LLP

(57) ABSTRACT

Topical formulations of L-ascorbic acid dissolved in a combination of a urea agent and a non-aqueous skin-compatible solvent are provided. The formulations are storage stable for an extended period of time without significant degradation of the L-ascorbic acid in the composition, are have desirable physical properties. The topical formulations can include high concentrations of the L-ascorbic acid. The topical formulations can include cinnamic acid or derivatives thereof as a penetration enhancer and stabilizing component of ascorbic acid. Topical compositions of this disclosure find use in treating or preventing a variety of cosmetic and/or dermatological conditions as well as to reduce the appearance of chronological and/or environmentally-caused skin aging.

24 Claims, No Drawings

(56) References Cited

U.S. PATENT DOCUMENTS

| | | | |
|---|---|---|---|
| 2009/0312724 | A1 | 12/2009 | Pipkin et al. |
| 2010/0189761 | A1 | 7/2010 | Friedman et al. |
| 2013/0131162 | A1 | 5/2013 | Kaplan |
| 2014/0142175 | A1 | 5/2014 | Kelada et al. |
| 2014/0147525 | A1 | 5/2014 | de Paula et al. |
| 2015/0250709 | A1* | 9/2015 | Gan ............... A61K 8/738 424/62 |
| 2016/0101029 | A1 | 4/2016 | Sanmiguel |
| 2016/0256369 | A1 | 9/2016 | Dutton et al. |
| 2016/0354328 | A1 | 12/2016 | Huang et al. |
| 2017/0224760 | A1 | 8/2017 | Garruto et al. |
| 2018/0071190 | A1 | 3/2018 | Albrecht et al. |
| 2018/0071203 | A1 | 3/2018 | Gan et al. |
| 2018/0116927 | A1 | 5/2018 | Chaudhuri |
| 2018/0228714 | A1 | 8/2018 | Thomas |
| 2018/0280286 | A1 | 10/2018 | Elsen-Wahrer et al. |
| 2019/0038689 | A1 | 2/2019 | Kalahasti et al. |
| 2019/0151214 | A1 | 5/2019 | Shaffer et al. |
| 2019/0192393 | A1 | 6/2019 | Chen et al. |
| 2019/0290639 | A1 | 9/2019 | Jackson |
| 2019/0336421 | A1 | 11/2019 | Maruyama |
| 2020/0121627 | A1* | 4/2020 | Park ............... A61K 8/41 |
| 2021/0228467 | A1 | 7/2021 | Baek |

FOREIGN PATENT DOCUMENTS

| | | | |
|---|---|---|---|
| CN | 109475472 A | | 3/2009 |
| CN | 106580798 B | | 8/2019 |
| CN | 110368326 | * | 10/2019 |
| EP | 1742710 B1 | | 6/2009 |
| JP | H05-229927 A | | 9/1993 |
| JP | H10509735 A | | 9/1998 |
| JP | 2008-088188 A | | 4/2008 |
| JP | 2013-170124 A | | 9/2013 |
| JP | 2017509705 A | | 4/2017 |
| WO | WO 93/19743 A1 | | 10/1993 |
| WO | WO 96/39119 A1 | | 12/1996 |
| WO | WO 1999/33439 A1 | | 7/1999 |
| WO | WO 2005/070380 A1 | | 8/2005 |
| WO | WO 2007/040027 A1 | | 4/2007 |
| WO | WO 2008/030308 A1 | | 3/2008 |
| WO | WO 2012/053009 A2 | | 4/2012 |
| WO | WO 2014/184173 A1 | | 11/2014 |
| WO | WO 2015/143399 A1 | | 9/2015 |
| WO | WO 2016/141315 A1 | | 9/2016 |
| WO | WO 2018/081779 A1 | | 5/2018 |
| WO | WO 2020/081868 A1 | | 4/2020 |
| WO | WO 2020/086820 A1 | | 4/2020 |
| WO | WO 2021/212077 A3 | | 6/2022 |

OTHER PUBLICATIONS

Kameyama, K. et al., "Inhibitory effect of magnesium l-ascorbyl-2-phosphate (VC-PMG) on melanogenesis in vitro and in vivo," Journal of the American Academy of Dermatology, vol. 34, Iss. 1, Jan. 1996, pp. 29-33.

Kim, S. et al., "Stabilization of L-ascorbic acid in cosmetic emulsions," Journal of Industrial and Engineering Chemistry, vol. 57, Jan. 25, 2018, pp. 193-198.

Maia, A.M. et al., "Validation of HPLC stability-indicating method for Vitamin C in semisolid pharmaceutical/cosmetic preparations with glutathione and sodium metabisulfite, as antioxidants," Talanta, vol. 71, Jun. 12, 2006, pp. 639-643.

PCT International Search Report and Written Opinion, PCT Application No. PCT/US2022/047305, Jan. 24, 2023, 18 pages.

PCT International Search Report and Written Opinion, PCT Application No. PCT/US2022/077119, Jan. 18, 2023, 19 pages.

PCT International Search Report and Written Opinion, PCT Application No. PCT/US2021/027835, Aug. 11, 2021, 17 pages.

PCT International Search Report and Written Opinion, PCT Application No. PCT/US2021/027834, Aug. 12, 2021, 14 pages.

PCT International Search Report and Written Opinion, PCT Application No. PCT/US2021/027832, May 11, 2022, 18 pages.

PCT International Search Report and Written Opinion, PCT Application No. PCT/US2021/027831, Aug. 11, 2021, 16 pages.

PCT International Search Report and Written Opinion, PCT Application No. PCT/US2021/027830, Aug. 11, 2021, 17 pages.

PCT International Preliminary Report on Patentability, PCT Application No. PCT/US2021/027830, Oct. 27, 2022, ten pages.

PCT International Search Report and Written Opinion, PCT Application No. PCT/US2021/027827, Jul. 16, 2021, 13 pages.

PCT International Preliminary Report on Patentability, PCT Application No. PCT/US2021/027827, Oct. 27, 2022, seven pages.

PCT International Search Report and Written Opinion, PCT/US2019/056822, dated Dec. 27, 2019, 16 pages.

Sarkar, R. et al., "Cosmeceuticals for Hyperpigmentation: What is Available?," Journal of Cutaneous and Aesthetic Surgery, vol. 6, No. 1, Jan. 2013, pp. 4-11.

Wikipedia, "Ferulic acid," Jan. 24, 2020, seven pages, [Online] Retrieved from the Internet <URL: https://en.wikipedia.org/w/index.php?title=Ferulic_acid&oldid=937396103>.

Ferreira, A.S. et al., "In Vivo Xylitol Primary Dermal Irritation and Phototoxicity Evaluation," Latin American Journal of Pharmacy, vol. 28, No. 2, Mar. 2009, pp. 192-195.

United States Office Action, U.S. Appl. No. 17/965,628, Apr. 19, 2023, 11 pages.

United States Office Action, U.S. Appl. No. 17/286,434, May 4, 2023, 17 pages.

European Patent Office, Extended European Search Report, European Patent Application No. 21788324.8, Aug. 6, 2024, 19 pages.

European Patent Office, Partial Supplementary European Search Report with Provisional Opinion, European Patent Application No. 21788324.8, May 16, 2024, 23 pages.

Glambrat. "Revolution: Good Vibes Lip Balm." INCIDecoder, Dec. 29, 2019, 5 pages, [Online] [Retrieved Apr. 7, 2025], Retrieved from the Internet <URL:https://incidecoder.com/products/revolution-good-b>.

Laboratoire Nuxe, "24HR Moisturizing Anti-Fatigue Concentrate," Record ID: 1287042, Mar. 2010, 5 pages.

Nurlaily, A. et al. "Comparative Antioxidant and Anti-Inflammatory Activity of Different Extracts of *Centella asiatica* (L.) Urban and Its Active Compounds, Asiaticoside and Madecassoside." Medicine & Health, vol. 7, No. 2, Jan. 2012, pp. 62-72.

Waterman, K. C. et al. "Accelerated Aging: Prediction of Chemical Stability of Pharmaceuticals." International Journal of Pharmaceutics, vol. 293, Nos. 1-2, Apr. 11, 2005, pp. 101-125.

* cited by examiner

STABILIZING VITAMIN C TOPICAL FORMULATIONS

CROSS REFERENCE TO RELATED APPLICATIONS

This application is a continuation application of co-pending Patent Cooperation Treaty (PCT) International Application No. PCT/US2021/027830, filed Apr. 16, 2021, which claims the benefit of U.S. Provisional Application No. 63/010,878, filed Apr. 16, 2020, the disclosures of which are hereby incorporated by reference in their entirety.

FIELD OF INVENTION

The present disclosure relates to stable compositions and methods for treating, preventing, or improving dermatocosmetic conditions, including reducing the appearance of skin aging. The present disclosure also relates to stable compositions and methods for accelerating and enhancing wound healing.

INTRODUCTION

Ascorbic acid (also commonly known as Vitamin C) is a potent antioxidant and is widely used in topical compositions to treat or prevent a range of cosmetic and/or dermatological conditions as well as to reduce the appearance of chronological and/or environmentally-caused skin aging, such as facial fine lines and wrinkles, dyschromia/uneven pigmentation, and dark circles under the eyes). Additionally, Vitamin C can help neutralize the damaging effects of free radicals and plays a role in stimulating the growth and bundling of collagen, important in maintaining skin elasticity.

Tyrosinase is a copper-containing enzyme that catalyzes the production of melanin and other pigments from tyrosine by oxidation. The antioxidant activity of ascorbic acid is reported to mediate, and thereby reduce (inhibit) the rate of melanogenesis. YK Choi et al., *Int J Dermatol*. Vol. 49, pp. 218-26 (2010).

The "gold standard" in cosmetic dermatology for skin lightening/brightening is hydroquinone (HQ). However, HQ can have side effects including mild burning, stinging, erythema (redness), and skin dryness. Vitamin C is also used to lighten the appearance of the skin—including for example, dark circles under the eyes—but with a more favorable safety profile (i.e., fewer side effects). See, e.g., LE Espinal-Perez et al, *Int J Dermatol*. Vol. 43, pp. 604-7 (2004) (93% improvement from use of 4% HQ versus 62.5% improvement from use of 5% Vitamin C; but 68.7% side-effects from HQ versus 6.2% from Vitamin C).

The scientific and patent literature describe Vitamin C topical products, especially water-containing formulations, as "unstable". Research and development activities seeking more stable topical Vitamin C formulations have focused on creating esterified derivatives (e.g., magnesium ascorbyl phosphate ("MAP") and ascorbyl-6-palmitate), using anhydrous carrier systems, adding antioxidants or other ingredients to Vitamin C formulations, and buffering Vitamin C formulations to a low pH. Representative prior art approaches, and their shortcomings, are discussed below.

There is a need for stabilized formulations containing higher concentrations of Vitamin C and methods of producing such formulations.

In topical compositions, the use of urea (and substituted ureas) is known, including for moisture retention (as a humectant), for keratolytic activity, as well as for penetration enhancement, both for itself and other active ingredients. At concentrations of lower than about 10%, urea acts as a moisturizer. At higher concentrations, from about 10% up to 40%, urea can be used to treat dry/rough skin conditions, including ichthyosis and psoriasis.

It is also known in the art that inclusion of urea at efficacious concentrations in aqueous topical compositions poses formulating challenges. Urea undergoes steady hydrolysis, producing ammonia and other amines, compounds that not only have an unpleasant odor but also tend to increase pH. Moreover, hydrolysis of urea in aqueous compositions can cause discoloration or other breakdown of the product, including phase separation.

There has been and remains a need for non-oily/non-greasy topical formulations that contain and maintain a high concentration of Vitamin C and efficacious amounts of urea without degradation, and concomitant decrease in biological activity. These needs are met by the high-potency Vitamin C concentrates of the present disclosure.

SUMMARY

Topical formulations of L-ascorbic acid dissolved in a combination of a urea agent and a non-aqueous skin-compatible solvent are provided. The formulations are storage stable for an extended period of time without significant degradation of the L-ascorbic acid in the composition, are have desirable physical properties. The topical formulations can include high concentrations of the L-ascorbic acid. The topical formulations can include cinnamic acid or derivatives thereof as a penetration enhancer and stabilizing component of ascorbic acid. Topical compositions of this disclosure find use in treating or preventing a variety of cosmetic and/or dermatological conditions as well as to reduce the appearance of chronological and/or environmentally-caused skin aging.

DETAILED DESCRIPTION

This disclosure provides topical formulations of L-ascorbic acid dissolved in a combination of a urea agent and a non-aqueous skin-compatible solvent. The formulations are storage stable for an extended period of time without undesirable discoloration or significant degradation of the L-ascorbic acid in the composition. This disclosure provides particular topical formulations which have been developed and optimized to provide skin compatibility and desirable physical properties.

Topical compositions of this disclosure find use in treating or preventing a variety of cosmetic and/or dermatological conditions as well as to reduce the appearance of chronological and/or environmentally-caused skin aging, such as facial fine lines and wrinkles, dyschromia or uneven pigmentation, and dark circles under the eyes. Non-limiting examples of dermatocosmetic conditions that may be improved by topical application of the compositions of the present disclosure include: keratoses, melasma, lentigines, liver spots, inflammatory dermatoses (including eczema, acne, psoriasis), and xeroses (also known in the art as dry skin or pruritus). Topical application can be accomplished by use of a biocompatible gel, which may be provided in the form of a patch, or by use of a cream, foam, and the like. Several gels, patches, creams, foams, and the like appropriate for application to wounds.

In some embodiments, formulations of the present disclosure include the ingredients: (i) 5 to 28% by weight ascorbic acid; and (ii) urea agent; and (iii) cinnamic acid dissolved in (iv) a non-aqueous skin-compatible solvent.

The present inventor has discovered that the formulations of the present disclosure provides the basis for enhancement and acceleration of topical wound healing. Thus, the inventors found that the formulations can be applied topically to facilitate wound healing.

The present inventor has discovered that a urea agent dissolved in a non-aqueous solvent provides for enhanced solubility and penetration of the ascorbic acid in the non-aqueous solvent.

The present inventor has discovered that cinnamic acids or derivatives thereof, such as ferulic acid, in addition to ascorbic acid and urea in a non-aqueous solvent, provide for enhanced stabilizing effects in the formulations of the present disclosure. Thus, incorporation of cinnamic acids and derivatives are penetration enhancers that provide for enhanced stability of ascorbic acid and a urea agent in a non-aqueous formulation.

Ascorbic Acid

This disclosure provides formulations that include combination of particular amount of a urea agent in a non-aqueous skin-compatible solvent which together can provide for dissolution of particular amounts of ascorbic acid and which produce skin-compatible liquid compositions in which the ascorbic acid is substantially stable to decomposition. In some embodiments, the amounts of ascorbic acid stably dissolved in the composition are greater than would otherwise be possible without the particular combinations of ingredients provided by the disclosure.

The terms "ascorbic acid", "L-ascorbic acid" and "vitamin C" are used interchangeably herein, and refer to the naturally occurring vitamin of CAS Registry Number: 50-81-7. Any convenient form of ascorbic acid can be utilized in the subject formulations. In some embodiments, the ascorbic acid used in the high potency Vitamin C concentrate of the present disclosure is a powder.

In certain embodiments, the ascorbic acid material used in preparing the subject compositions is composed of granular particles. Such a particulate powder has a particle size (e.g., mean particle size) of less than about 25 microns, such as less than about 20 microns, and more preferably less than about 12.5 microns, e.g., as measured by a Hagman gauge. In some embodiments, all of the ascorbic acid powder used in preparing the subject compositions is capable of passage through a No. 100 U.S. Standard Sieve, a standard testing procedure used by the US Pharmacopoeia. In some embodiments, 80% or more (such as 90% or more, or 100%) of ascorbic acid powder used in preparing the subject composition is capable of passage through a No. 325 U.S. Standard Sieve. For example, one powder meeting the above criterion is Ascorbic Acid Ultra-Fine Powder from DSM Nutritional Products LLC, Parsippany, NJ. Previously, this product was available as Product Code No. 6045653 from Roche Vitamins and Fine Chemicals.

In some embodiments, the amount of ascorbic acid in the subject composition is at least about 5% by weight, such as at least about 10% by weight, at least about 12% by weight, at least about 15% by weight, at least about 20% by weight, or at least about 25% by weight. In some embodiments, the subject composition includes about 28% by weight or less of ascorbic acid in the non-aqueous solvent solution, such as about 25% by weight or less. In certain embodiments, the non-aqueous solvent is 1,3-propanediol. In particular embodiments, the amount of ascorbic acid in the subject composition is between about 10% by weight and about 20% by weight, or between about 12% by weight and about 28% by weight, such as between about 15% by weight and about 28% by weight, or between about 20% by weight and about 28% by weight. In some embodiments, the amount of ascorbic acid in the subject composition is about 5%, about 10%, about 15%, about 20%, or about 25% by weight.

In some embodiments, the amount of ascorbic acid in the subject composition is about 5%, about 6%, about 7%, about 8%, about 9%, about 10%, about 11%, about 12%, about 13%, about 14%, about 16%, about 17%, about 18%, about 19%, about 20%, about 21%, about 22%, about 23%, about 24%, about 25%, about 26%, about 27%, about 28%, about 29%, or about 30% by weight.

In particular embodiments, the amount of ascorbic acid in the subject composition is between about 10% by weight and about 20% by weight (e.g., about 10%, about 15%, or about 20%) where the ratio of ascorbic acid to urea agent (% wt ratio) is 1.8 to 2.2, such as a ratio of 2 (i.e., 2:1).

In particular embodiments, the amount of ascorbic acid in the subject composition is between about 25% by weight and about 28% by weight (e.g., about 25%, about 26%, about 27% or about 28%) where the ratio of ascorbic acid to urea agent (% wt ratio) is 1.0 to 1.3, such as a ratio of 1.25 (i.e., 1.25:1) or a ratio of 1.0 (i.e., 1:1).

In general, the amounts of ascorbic acid in a composition are calculated relative to the solution phase based on the non-aqueous solvent. See e.g., Formulations 1, 3, 4, 6 and 7 of Table 3. However, the amounts of ascorbic acid and other ingredients relative to the emulsion composition as a whole can readily be calculated by the skilled artisan. Formulations 2 and 5 of Table 3 show exemplary emulsion compositions where the % by weight values shown are relative to the total emulsion composition. It is understood that, in some cases, these concentrate solutions having particular amounts of ascorbic acid can be combined with an immiscible ingredient (e.g., a oil component) and an emulsifying agent to produce an emulsion composition (e.g., as described below).

Urea Agent

The formulations of the present disclosure include a urea agent in an amount sufficient to enhance the solubility of ascorbic acid in the non-aqueous skin compatible solvent and to provide a stable solution. The inventor discovered that particular amounts of urea agent can be added to a non-aqueous solvent to provide stable solutions of ascorbic acid at various desired concentration levels. These amounts of urea agent are selected based on observations regarding the maximum amount of ascorbic acid that can be stably dissolved in the particular non-aqueous solvent, and minimum amounts of urea agent that should be included to provide a stable ascorbic acid solution.

Urea agents of interest include, but are not limited to, urea and substituted urea, such as alkyl substituted urea, more particularly mono-substituted or di-substituted alkyl urea (e.g., hydroxyalkyl urea). In some embodiments, the urea agent is a hydroxyalkyl urea, such as hydroxyethyl urea. The urea agent ingredient used in the subject formulations can be a combination of urea and/or substituted urea. For example, the urea agent can be a combination of urea and hydroxyethyl urea. In certain embodiments, the urea agent is urea. In certain embodiments, the urea agent is hydroxyethyl urea.

In some embodiments, the amount of urea in the high-potency vitamin C compositions of this disclosure is defined as a function of the concentration of L-Ascorbic Acid ("AA"). For AA concentrations exceeding the maximum solubility of ascorbic acid in the neat non-aqueous solvent (Z %), as a first step, subtract Z from the desired amount of AA in the concentrate solution. As a second step, multiply the difference from the first step by 1.25. The minimum amount (% wt) of urea agent to be included in the non-aqueous solvent based compositions can be calculated by the formula: {concentration of AA-Z}*1.25.

For compositions based on 1,3-propanediol as solvent, the maximum solubility of ascorbic acid (AA) in neat 1,3-propanediol was observed to be 12% by weight. Accordingly, for AA concentrations exceeding 12%, as a first step, subtract 12 from the desired amount of AA in the concentrate. As a second step, multiply the difference from the first step by 1.25. The minimum amount (% wt) of urea agent to be included in the 1,3-propanediol based compositions can be calculated by the formula: {concentration of AA-12}*1.25. See Table 1.

TABLE 1

Minimum urea agent in 1,3-propanediol compositions
{concentration of AA − 12} * 1.25

| ascorbic acid (% wt) | Minimum urea agent (% wt) |
|---|---|
| 13 | 1.25 |
| 14 | 2.5 |
| 15 | 3.75 |
| 16 | 5 |
| 17 | 6.25 |
| 18 | 7.5 |
| 19 | 8.75 |
| 20 | 10 |
| 21 | 11.25 |
| 22 | 12.5 |
| 23 | 13.75 |
| 24 | 15 |
| 25 | 16.25 |
| 26 | 17.5 |
| 27 | 18.75 |
| 28 | 20 |

For example, for compositions including 15% by weight ascorbic acid, at least about 4% urea is included in the 1,3-propanediol solvent. For compositions including 20% by weight ascorbic acid, at least about 10% urea is included in the 1,3-propanediol solvent. For compositions including 25% by weight ascorbic acid, at least about 16% urea is included in the 1,3-propanediol solvent. In some embodiments, additional amounts of urea agent can be included up to a maximum amount of 20% by weight, to provide desirable physical properties, in combination with additional optional minor ingredients.

In some embodiments, the subject composition includes about 13 to 19% by weight ascorbic acid, about 2 to about 9% by weight urea agent and 1,3-propanediol. In some embodiments, the subject composition includes about 15% by weight ascorbic acid, about 2 to about 9% by weight urea agent (e.g., about 4%, about 5%, about 6%, about 7% or about 8%) and 1,3-propanediol. In certain embodiments, the subject composition includes about 15% by weight ascorbic acid, about 8% by weight urea agent and 1,3-propanediol.

In some embodiments, the subject composition includes about 20 to 24% by weight ascorbic acid, about 10 to about 15% by weight urea agent and 1,3-propanediol. In some embodiments, the subject composition includes about 20% by weight ascorbic acid, about 10 to about 15% by weight urea agent (e.g., about 10%, about 11%, about 12%, about 13%, about 14% or about 15%) and 1,3-propanediol. In certain embodiments, the subject composition includes about 20% by weight ascorbic acid, about 10% by weight urea agent and 1,3-propanediol.

In some embodiments, the subject composition includes about 25 to 28% by weight ascorbic acid, about 16 to about 20% by weight urea agent and 1,3-propanediol. In some embodiments, the subject composition includes about 25% by weight ascorbic acid, about 16 to about 20% by weight urea agent (e.g., about 16%, about 17%, about 18%, about 19%, or about 20%) and 1,3-propanediol. In certain embodiments, the subject composition includes about 25% by weight ascorbic acid, about 20% by weight urea agent and 1,3-propanediol.

In some embodiments, the subject composition includes a combination of

Cinnamic Acids and Derivatives Thereof

The formulations of the present disclosure also include a cinnamic acid and sources thereof, which are known to work synergistically with ascorbic acid to provide additional antioxidant protection to skin. Cinnamic acids of interest and sources thereof include, but are not limited to, ferulic acid, caffeic acid and coumaric acid. In some embodiments, the cinnamic acid is ferulic acid. The cinnamic acid ingredient used in the subject formulation can be a combination of ferulic acid and/or substituted cinnamic acids. For example, the cinnamic acid agent used can be a combination of ferulic acid and caffeic acid.

In some embodiments, the subject composition includes about 0.1% to 2% by weight of cinnamic acid (e.g., about 0.1%, about 0.5%, about 1%, about 1.5%, or about 2%).

The formulations of the present disclosure include cinnamic acid and derivatives thereof (e.g., ferulic acid, caffeic acid, coumaric acid, sinapinic acid, and other phenolic cinnamic acids), cis and trans isomers thereof, salts thereof, equivalents thereof.

In some embodiments, the composition of the present disclosure includes 0.1% or more by weight of cinnamic acid or derivatives thereof. In some embodiments, the composition includes 0.1% to 5.0% by weight of cinnamic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of cinnamic acid or derivatives thereof. In some embodiments, the composition includes about 0.1 to 5.0% by weight of cinnamic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of cinnamic acid or derivatives thereof).

Suitable cinnamic acids or derivatives thereof that can be used in the composition of the present disclosure are found in U.S. Pat. No. 6,596,761, which is hereby incorporated by reference in its entirety.

The term "derivatives of caffeic acid, coumaric acid, ferulic acid" is to be understood as meaning their cosmetically or pharmacologically acceptable esters, salts and base adducts, in particular those such as are described above for the cinnamic acid derivatives.

Ferulic Acid and Derivatives Thereof

In some embodiments, the cinnamic acid derivative is a ferulic acid. Ferulic acid is an antioxidant that increases AA's photoprotective effect on skin. The present inventors found that ferulic acid can stabilize and solubilize AA in non-aqueous systems. In some embodiments, the composition of the present disclosure includes ferulic acid or derivatives thereof. In some embodiments, the ferulic acid is E-ferulic acid. In some embodiments, the ferulic acid is Z-ferulic acid. In some embodiments, the ferulic acid is a mixture of E- and Z-ferulic acid.

Ferulic acid, when combined with Vitamin C and/or Vitamin A, can protect vitamin A and vitamin C thereby improving the photoprotective action of these vitamins. In combination with vitamin C, ferulic acid can provide two to four times as much photoprotection against ultraviolet radiation thus helping to minimize the harmful effects (e.g., erythema or formation of sunburn cells) caused by ultraviolet radiation. Ferulic acid can also improve the chemical stability of vitamin C and/or vitamin E to enhance a synergistic and longer lasting photoprotective effect.

In some embodiments, ferulic acid is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of ferulic acid by enhancing skin penetration.

In some embodiments, the composition of the present disclosure includes 0.1% or more by weight of ferulic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of ferulic acid or derivatives thereof. In some embodiments, the composition includes about 0.1 to 5.0% by weight of ferulic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of ferulic acid or derivatives thereof).

In certain embodiments, the composition includes 2% or less by weight of the ferulic acid, such as 1.5% or less, 1.0% or less (e.g., about 1% by weight), or 0.5% or less (e.g., about 0.5% by weight) of the ferulic acid.

In some embodiments, ferulic acid (e.g., 4-hydroxy-3-methoxy-cinnamic acid, caffeic acid 3-methyl ether) is characterized by the structural formula

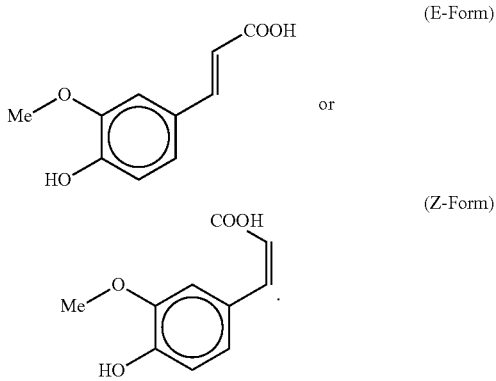

Caffeic Acid and Derivatives Thereof

In some embodiments, the cinnamic acid derivative is a caffeic acid. Caffeic acid is an antioxidant that increases AA's photoprotective effect on skin. It can also stabilize AA in aqueous systems. In some embodiments, the composition of the present disclosure includes caffeic acid or derivatives thereof.

In some embodiments, caffeic acid is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of caffeic acid by enhancing skin penetration.

In some embodiments, the composition of the present disclosure includes 0.1% or more by weight of caffeic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of caffeic acid or derivatives thereof. In some embodiments, the composition includes about 0.1 to 5.0% by weight of caffeic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of caffeic acid or derivatives thereof).

In some embodiments, caffeic acid comprises the structure:

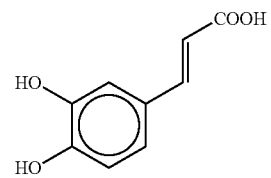

In some embodiments, the cinnamic acid derivative is a combination of ferulic acid and caffeic acid. In some embodiments, the cinnamic acid derivative is trans-ferulic acid and caffeic acid.

Coumaric Acid and Derivatives Thereof

In some embodiments, the cinnamic acid derivative is a coumaric acid. Coumaric acid is an antioxidant that increases AA's photoprotective effect on skin. It can also stabilize AA in aqueous systems. In some embodiments, the composition of the present disclosure includes coumaric acid or derivatives thereof. In some embodiments, coumaric acid comprises p-coumaric acid.

In some embodiments, coumaric acid is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of coumaric acid by enhancing skin penetration.

In some embodiments, the composition of the present disclosure includes 0.1% or more by weight of coumaric acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of coumaric acid or derivatives thereof. In some embodiments, the composition includes about 0.1 to 5.0% by weight of coumaric acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of coumaric acid or derivatives thereof).

Sinapinic Acid (e.g., Hydroxycinnamic Acids) and Derivatives Thereof

In some embodiments, the cinnamic acid derivative is sinapinic acid or derivatives thereof. Sinapinic acid is an antioxidant that increases AA's photoprotective effect on skin. It can also stabilize AA in aqueous systems. In some embodiments, the composition of the present disclosure includes sinapinic acid or derivatives thereof.

In some embodiments, sinapinic acid or derivatives thereof is readily soluble in non-aqueous solvents. In some embodiments, the non-aqueous solvent is one or more of 1,3 propanediol, 1,2 propanediol, 1,3 butanediol, and dimethyl isosorbide. In some embodiments, isosorbide can increase the effectiveness of sinapinic acid or derivatives thereof by enhancing skin penetration.

In some embodiments, the composition of the present disclosure includes 0.1% or more by weight of sinapinic acid or derivatives thereof. In some embodiments, the composition includes 0.2% or more, 0.3% or more, 0.4% or more, 0.5% or more, 0.6% or more, 0.7% or more, 0.8% or more, 0.9% or more, 1.0% or more, 1.1% or more, 1.2% or more, 1.3% or more, 1.4% or more, 1.5% or more, 1.6% or more, 1.7% or more, 1.8% or more, 1.9% or more, or 2.0% or more by weight of sinapinic acid or derivatives thereof. In some embodiments, the composition includes about 0.1 to 5.0% by weight of sinapinic acid or derivatives thereof (e.g., 0.1% to 0.5%, 0.5% to 1.0%, 1.0% to 1.5%, 1.5% to 2.0%, 2.0% to 2.5%, 2.5% to 3.0%, 3.0% to 3.5%, 3.5 to 4.0%, 4.0 to 4.5%, or 4.5% to 5.0% by weight of sinapinic acid or derivatives thereof).

In some embodiments, the sinapinic acid includes the general formula:

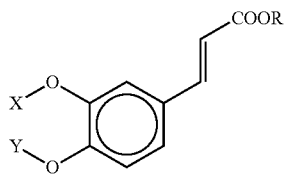

and/or active amounts of cinnamic acid derivatives of the formula:

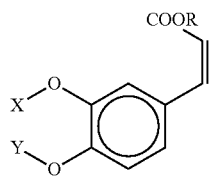

wherein the groups X, Y an R independently of one another can be chosen from the group consisting of H and branched and unbranched alkyl having 1-18 C atoms, for example 1-6 C atoms, can be used.

Skin Compatible Solvent

In addition to the urea agent and cinnamic acid (e.g., as described herein), the high-potency Vitamin C formulations of the present disclosure contain, as an essential ingredient, at least one non-aqueous skin-compatible solvent. A skin compatible solvent is a solvent that does not cause irritation or sensitization when applied topically to the skin. Non-aqueous skin-compatible solvents of interest include polyols, C(2-6) alkanediols, glycol ethers, dimethyl ethers, and combinations thereof.

In some embodiments, the solvent is a skin compatible polyol. A polyol is an organic alcohol solvent having two or more hydroxy groups. In some embodiments, the polyol solvent is a C(3-6)polyol. In some embodiments, the polyol solvent is a polyether polyol. In some embodiments, the polyol solvent is a polyester polyol. Skin compatible polyols of interest include, but are not limited to, glycerol (1,2,3-propanetriol); diglycerol; propylene glycol (1,2-propanediol); dipropylene glycol; 1,3-propanediol; butylene glycol (1,3-butanediol); 1,2-butanediol; pentylene glycol (1,2-pentanediol); 1,5-pentanediol; 1,2-hexanediol; 1,6-hexanediol; 1,2,3-hexanetriol, 1,2,6-hexanetriol; ethoxydiglycol; and dimethyl isosorbide. In some embodiments, the solvent is a glycol ether, a dimethyl ether, or a combination thereof. A preferred skin-compatible solvent is 1,3-propanediol, commercially available from DuPont Tate & Lyle BioProducts LLC under the tradename ZEMEA®. In some embodiments, the solvent is a mixture of 1,3 propanediol and 1,2 hexanediol.

In some embodiments, the subject composition includes about 10 to 99% by weight (e.g. about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, or about 99% or more) of a non-aqueous skin compatible solvent. In some embodiments, the subject composition includes about 1 to 30% by weight of an agent (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%) and 10 to 99% polyol. In some embodiments, the subject composition includes about 1 to 30% by weight of an agent (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%) and 10 to 99% polyol and one or more additional skin compatible solvents.

Additional Components

A formulation may contain one or more (optional) additional ingredients. Any convenient ingredient known to the skilled artisan to provide cosmetic/aesthetic benefits can be utilized in the subject formulations. Such cosmetic/aesthetic benefits include, but are not limited to, reducing the appearance of fine lines/wrinkles, improving skin barrier function (by reducing the rate/extent of trans-epidermal water loss), making the skin feel smoother/more supple/softer, creating the appearance of more even skin tone (reducing dyschromia) and/or "glow"/radiance (also described in the art as "brightness").

In some embodiments, the composition further includes one or more optional additional components (e.g., as described herein). In some embodiments, the one or more optional additional components are selected from tocopherols, tocotrienols (e.g., alpha, beta, delta and gamma tocopherols or alpha, beta, delta and gamma tocotrienols), azelaic acid, hydroxy acids (e.g., salicylic acid), panthenol, *Pinus pinaster* bark extract, emulsifying agent, hyaluronic acid complex, madecassoside, madecassoside asiaticoside, acetyl zingerone, bakuchiol, and bis-ethylhexyl hydroxydimethoxy benzylmalonate.

Each optional additional component (e.g., as described herein) may be present in an amount of 10% or less by weight of the composition, such as 9% or less, 8% or less, 7% or less, 6% or less, 5% or less, 4% or less, 3% or less, 2% or less, 1% or less by weight. In some embodiments the total amount of the one or more optional additional components (e.g., as described herein) in the composition 10% or less by weight, such as 9% or less, 8% or less, 7% or less, 6% or less, 5% or less, 4% or less, 3% or less, 2% or less, 1% or less by weight.

In some embodiments, the composition further includes 10% or less by weight in total of one or more optional additional components selected from an antioxidant, a skin lightening agent, and a moisturizing agent.

Tocopherol or Tocotrienol Agent

In some embodiments, the composition further includes optional additional component that is a tocopherol or tocotrienol agent. In some embodiments, the tocopherol or tocotrienol agent is a form of Vitamin E selected from alpha, beta, delta and gamma tocopherols and alpha, beta, delta and gamma tocotrienols, and combinations thereof. In some embodiments, the tocopherol or tocotrienol is alpha-tocopherol.

In some embodiments, the tocopherol or tocotrienol agent is present in the composition in an amount of 2% or less by weight, such as 1.5% or less, 1% or less, or 0.5% or less by weight.

In some embodiments of any one of the formulations described herein, the formulation excludes tocopherol or tocotrienol agents, e.g., or precursors thereof having vitamin E activity. In certain embodiments of any one of the formulations described herein, the formulation excludes vitamin E acetate.

Antioxidants

In certain embodiments, the formulation contains a secondary antioxidant (i.e., in addition to Vitamin C or the optional additive tocopherol or tocotrienol agent).

In some embodiments, secondary antioxidants include terpenoid antioxidants, and benzoic acid derivatives (e.g., p-hydroxy benzoic acid, gallic acid, or protocatechuic acid). *Pinus Pinaster* Bark/Bud Extract (available under the tradename Pycnogenol® from DKSH North America, Inc., or from Res Pharma Industriale under the tradename Pantrofina® Skin360) contains these cinnamic acid derivatives and benzoic acid derivatives, and is, therefore, a preferred secondary antioxidant.

In some embodiments, the secondary antioxidant is zingerone or acetyl zingerone. In some embodiments, the secondary antioxidant is bakuchiol (10309-37-2) a natural terpenoid antioxidant. In some embodiments, the secondary antioxidant is bis-ethylhexyl hydroxydimethoxy benzylmalonate (HDBM).

The secondary antioxidant, when included, is preferably present in an amount in the range of 0.1 to 3%, more preferably 0.1 to 2% by weight of the composition, such as 0.1 to 1% by weight, 0.1 to 0.5% by weight, e.g., about 0.2%, about 0.3%, about 0.4% or about 0.5% by weight. In some embodiments, the secondary antioxidant is acetyl zingerone.

In some embodiments, the antioxidant is suitable for boosting photoprotection from UVA radiation. Additional non-limiting examples of antioxidants include polydatin, phloretin, resveratrol, ferulic acid, and a mixture thereof. In some embodiments, the antioxidant can be combined with one or more UV filters, for example organic UV filters, in a cosmetically acceptable carrier. The UV filter(s) may be UVB filters, UVA filters (UVA1 and/or UVA2 filters), and/or inorganic UV filters (UVA and/or UVB filters).

Skin Lightening Agents

In certain embodiments, the formulation contains a secondary skin lightening agent (e.g., as defined herein) (i.e., in addition to Vitamin C). Skin lightening agents which may be included in compositions of the present disclosure include, but are not limited to: hydroquinone and its derivatives, including, for example, its monomethyl and monobenzyl ethers; licorice root (*Glycyrrhiza glabra*) extract; azelaic acid; kojic acid; arbutin; retinoids (including all-trans-retinoic acid, adapalene and tazarotene); alpha hydroxy acids, in particular citric acid, lactic acid, and glycolic acid; ellagic acid; gluconic acid; gentisic acid (2,5-dihydrobenzoic acid); 4-hydroxy benzoic acid; salts and esters of the above-mentioned acids, including ammonium lactate and sodium lactate; N-acetyl glucosamine; aloesin, a hydroxymethyl chromone isolated from aloe vera; Vitamin B3 compound or its derivative—niacin, nicotinic acid, niacinamide. Epigallocatechin 3-O-gallate (EGCG), and other catechin constituents of tea extracts, in particular green tea; extract of soybean oil (*Glycine soja*), including isoflavones; hydroxystilbene; butyl hydroxy anisole; and butyl hydroxy toluene may also be utilized as a skin lightening agent. In some embodiments, the additional skin lightening agent is azelaic acid or arbutin.

The skin lightening agent, when included, is preferably present in an amount in the range of 0.1 to 10%, more preferably 0.2 to 5% by weight of the composition, such as 0.2 to 4% by weight, 0.2 to 3% by weight, or 0.2 to 2% by weight. In certain embodiments, the secondary skin lightening agent is soluble and may be added directly to the high Vitamin C (>15%) concentrate of the present invention. The secondary skin lightening agent may also be encapsulated using techniques known to the person having ordinary skill in the art.

Hydroxy Acids

In some embodiments, formulation contains a hydroxy acid, e.g., a small molecule compound including a carboxylic acid and a hydroxy group. The acid may be an alkyl carboxylic acid or a benzoic acid. The hydroxy group can be a phenol or an alkyl alcohol. In certain embodiments, the hydroxy acid is an alpha-hydroxy carboxylic acid. In certain embodiments the hydroxy acid contains 2-12 carbon atoms, such as 2-6 or 2-4 carbons. Hydroxy acids of interest include, but are not limited to, glycolic acid, lactic acid, mandelic acid, salicylic acid, capryloyl salicylic acid, salicyloyl phytosphingosine, gluconolactone, lactobionic acid, maltobionic acid, and combinations thereof.

Anti-Inflammatory

In some embodiments, formulation contains an anti-inflammatory agent as an additional ingredient. In some embodiments, the anti-inflammatory agent is madecassoside, madecassoside asiaticoside, or madecassic acid. The anti-inflammatory agent, when included, is preferably present in an amount in the range of 0.1 to 2%, more preferably 0.1 to 1% by weight of the composition, such as 0.1 to 0.5% by weight, or 0.1 to 0.2% by weight. In some embodiments, madecassoside is included in an amount in the range of 0.1 to 0.5%, such as about 0.1% or about 0.2% by weight.

Exemplary Topical Formulations

In some embodiments, the topical composition includes: a) 5% to 28% by weight ascorbic acid; and b) 5% to 20% by weight of a urea agent, wherein the ratio of ascorbic acid to urea agent is between about 1.0 and about 3.5; dissolved in a non-aqueous skin-compatible solvent selected from polyol, C(2-6) alkanediol, glycol ether, dimethyl ether, or a combination thereof. In general, the ascorbic acid is dissolved at a concentration (AA) that is above its maximum concentration in the solvent alone (X), and the urea is dissolved at a concentration that is at least about (AA−X)*1.25. In some embodiments, the urea is dissolved at a concentration that is about (AA−X)*1.25. In some embodiments, the urea is dissolved at a concentration that is (AA−X)*1.25±1% by weight, such as (AA−X)*1.25±0.5% by weight.

In some embodiments, the ratio of ascorbic acid to urea agent in the composition is 1.8 to 2.2. In some embodiments, the topical composition includes about 15% by weight ascorbic acid; about 8% by weight urea agent; a solvent that includes 1,3-propanediol and/or 1,2-hexanediol; and one or more optional additional components. In certain embodiments, the one or more optional additional component includes acetyl zingerone. In certain embodiments, the one or more optional additional component is a tocopherol or tocotrienol (e.g., as described herein).

In some embodiments, the ratio of ascorbic acid to urea agent in the composition is 1.8 to 2.2. In some embodiments, the topical composition includes about 20% by weight ascorbic acid; about 10% by weight urea agent; a solvent that is 1,3-propanediol; and one or more optional additional components.

In some embodiments, the ratio of ascorbic acid to urea agent in the composition is 1.8 to 2.2. In some embodiments, the topical composition includes about 10% by weight ascorbic acid; about 5% by weight urea agent; a solvent that is 1,3-propanediol; and one or more optional additional components. In certain embodiments, the one or more optional additional components include *Pinus pinaster* bark extract. In some embodiments, the composition includes 2% or less by weight of the *Pinus pinaster* bark extract, such as 1.5% or less, 1% or less, or 0.5% or less (e.g., about 0.5% by weight) of the *Pinus pinaster* bark extract.

In some embodiments, the ratio of ascorbic acid to urea agent in the composition is a ratio from 1.0 to 1.3, such as 1.25. In some embodiments, the topical composition includes about 25% by weight ascorbic acid; about 20% by weight urea agent; a solvent that is 1,3-propanediol; and one or more optional additional components. In certain embodiments, the one or more optional additional components include a hydroxy acid, such as glycolic acid, lactic acid, mandelic acid, salicylic acid, capryloyl salicylic acid, salicyloyl phytosphingosine, gluconolactone, lactobionic acid, maltobionic acid, or combinations thereof. In some embodiments, the hydroxy acid is salicylic acid. In some embodiments, the composition includes 3% or less by weight of the hydroxy acid, such as 2% or less, or 1% or less (e.g., about 2% by weight) of the hydroxy acid.

In some embodiments, the ratio of ascorbic acid to urea agent in the composition is about 1 (e.g., 1:1). In some embodiments, the topical composition includes about 5% by weight ascorbic acid; about 5% by weight urea agent; a solvent that is 1,3-propanediol; and one or more optional additional components. In certain embodiments, the one or more optional additional components include panthenol. In some embodiments, the composition includes 10% or less by weight of the panthenol, such as 5% or less, 4% or less, 3% or less, 2% or less, or 1% or less (e.g., about 4% by weight) of panthenol. In some embodiments, the composition includes about 1% to about 6% by weight of the panthenol, such as about 6%, about 5%, about 4%, about 3%, about 2%, or about 1% by weight of panthenol. In certain embodiments, the one or more optional additional components include hyaluronic acid complex. In some embodiments, the composition includes 2% or less by weight of the hyaluronic acid complex, such as 1.5% or less, 1% or less, or 0.5% or less (e.g., about 1% by weight) of the hyaluronic acid complex.

In some embodiments, the formulations of the present disclosure are concentrates which are generally: free of silicones, and "substantially free" of water. By "substantially free" of water is meant that (i) water is not intentionally added to the concentrate, and (ii) the amount of water in the concentrate is less than about 2% by weight of the concentrate, preferably less than 1% by weight, more preferably less than about 0.5%, and still more preferably less than about 0.1%. In certain embodiments, the concentrate is also free of oils or lipids.

Emulsion Compositions

It is understood that any of the non-aqueous liquid compositions having particular amounts of ascorbic acid (e.g., as described herein) can be combined with an immiscible phase or ingredient (e.g., an oilcomponent) to produce an emulsion composition. In some embodiments, the non-aqueous liquid composition that makes up the first phase of an emulsion composition is referred to as a concentrate. The liquid concentrate can be mixed with one or more additional components (e.g., an immiscible oil phase or component and an optional emulsifying agent) to produce an emulsion. A variety of methods and ingredients for preparing emulsions are available and can be used in the subject emulsion compositions.

In some embodiments, an emulsion composition of this disclosure is referred to as a gel.

Any convenient oils and lipids can be utilized in the oil component of the subject emulsions. An oil component or oil phase refers to any phase that is immiscible with the non-aqueous liquid composition. In some embodiments, the oil component is silicone-based, e.g., includes a silicone polymer. In some embodiments, the oil component includes a silicone oil or silicone elastomer, such as a polyorganosiloxane. In some embodiments, the silicone polymers have dual characteristics, and can be used as emulsifiers and/or act as the continuous/dispersed phase of the emulsion composition.

Oils and lipids of interest include, but are not limited to, silicone oils, linseed oil, tsubaki oil, macadamia nut oil, corn oil, mink oil, olive oil, avocado oil, sasanqua oil, castor oil, safflower oil, apricot oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, teaseed oil, evening primrose oil, eggyoke oil, neetsfoot oil, liver oil, triglycerine, glycerine trioctanate, pentaerythritol tetraoctanate, glycerine triisopalmitate, cholesterol, free fatty acids, and combinations thereof.

Any convenient emulsifying agents or emulsifiers can be utilized in the preparation of the subject emulsions to stabilize the composition and prevent separation of the oil component from the solvent solution (e.g., the non-aqueous liquid composition). Exemplary emulsifying agents include but are not limited to polysorbates, laureth-4, potassium cetyl sulfate, and silicone and silicone-elastomer-based emulsifiers and emulsifying blends. In some embodiment, a surfactant such as a monoglyceride, sorbitan fatty acid ester, or polyglycerine fatty acid ester, polyoxyethylene hardened castor oil, polyoxyethylene fatty acid ether, is added thereto in a small amount, and the stability is further improved.

Storage Stability

High-potency Vitamin C formulations of the present disclosure are capable of maintaining at least 90% of the starting ascorbic acid content when the concentrate is stored at room temperature for 12 months or longer.

The amount of ascorbic acid content in a composition can be determined using a wide range of techniques including, but not limited to: titrimetric, spectrophotometric, electrochemical, fluorimetric, enzymatic and chromatographic. Methods for determining ascorbic acid content in a topical formulation can be complicated/confounded by the presence of excipients or other antioxidant agents (e.g., agents for stabilizing Vitamin C), as well as degradation products. Of the above-listed methods, high performance liquid chromatography is preferred. See, A M Maia et al., "Validation of HPLC stability-indicating method for Vitamin C in semi-solid pharmaceutical/cosmetic preparations . . . " Talanta Vol. 71, pp. 639-643 (2007).

In some embodiments, the storage stable composition of this disclosure demonstrates less than 10 mol % degradation of the ascorbic acid after storage for 6 weeks or longer (e.g., 8 weeks or longer, 10 weeks or longer, 12 weeks or longer, 18 weeks or longer, 24 weeks or longer, 1 month or longer, 2 months or longer, 3 months or longer, 4 months or longer, 5 months or longer, 6 months or longer, 7 months or longer, 8 months or longer, 9 months or longer, 10 months or longer, 11 months or longer, 12 months or longer, 13 months or longer, 14 months or longer, 15 months or longer, 16 months or longer, or even longer) at 40° C.±2° C. in a sealed container, such as less than 9 mol %, less than 8 mol %, less than 7 mol %, less than 6 mol %, less than 5 mol %, less than 4 mol %, less than 3 mol %, less than 2 mol % degradation of the ascorbic acid initially present in the composition prior to storage.

In some embodiments, the storage stable composition of this disclosure demonstrates less than 10 mol % degradation of the ascorbic acid after storage for 4 weeks or longer (e.g., 6 weeks or longer, 8 weeks or longer, 10 weeks or longer, 12 weeks or longer, 18 weeks or longer, 24 weeks or longer, 1 month or longer, 2 months or longer, 3 months or longer, 4 months or longer, 5 months or longer, 6 months or longer, 7 months or longer, 8 months or longer, 9 months or longer, 10 months or longer, 11 months or longer, 12 months or longer, 13 months or longer, 14 months or longer, 15 months or longer, 16 months or longer, or even longer) at 45° C.±2° C. in a sealed container, such as less than 9 mol %, less than 8 mol %, less than 7 mol %, less than 6 mol %, less than 5 mol %, less than 4 mol %, less than 3 mol %, less than 2 mol % degradation of the ascorbic acid initially present in the composition prior to storage.

In some embodiments, the storage stable composition of this disclosure demonstrates less than 10 mol % degradation of the ascorbic acid after storage for 6 months or longer (e.g., 8 months or longer, 10 months or longer, 12 months or longer, 16 months or longer, 18 months or longer, or even longer) at 25° C.±2° C. in a sealed container or a multi-use container, such as less than 9 mol %, less than 8 mol %, less than 7 mol %, less than 6 mol %, less than 5 mol %, less than 4 mol %, less than 3 mol %, less than 2 mol % degradation of the ascorbic acid initially present in the composition prior to storage. In certain embodiments, the composition is stored in a sealed container. In certain embodiments, the composition is stored in a multi-use container.

In some embodiments, the storage stable composition of this disclosure demonstrates less than 20 mol % degradation of the ascorbic acid after storage for 12 months or longer (e.g., 16 months or longer, 18 months or longer, 24 months or longer, or even longer) at 40° C.±2° C. in a sealed container or a multi-use container, such as less than 15 mol %, less than 12 mol %, less than 10 mol %, less than 8 mol %, less than 6 mol %, less than 6 mol %, less than 4 mol %, less than 3 mol %, less than 2 mol % degradation of the ascorbic acid initially present in the composition prior to storage. In certain embodiments, the composition is stored in a sealed container. In certain embodiments, the composition is stored in a multi-use container.

Containers

In some embodiments, the high potency Vitamin C concentrate of the disclosure is administered with a second non-aqueous formulation (i.e., oil, ester and/or silicone carrier). The two compositions can be pre-filled into a "dual-chamber" container—a pump container in which two formulations are stored separately prior to dispense—with a high-potency Vitamin C concentrate of the invention in a first chamber, and a non-aqueous formulation in a second chamber. Some dual-chamber containers have two separate actuators/pumps, each having an orifice for dispensing one of the two formulations. Other dual-chamber containers contain two pumps and one actuator from which the two formulations are dispensed—either side-by-side (e.g., through two orifices), or from a single shared orifice. A non-limiting example of a dual-chamber container is described in U.S. Pat. No. 6,462,025.

Any containers suitable for storing and/or dispensing the subject formulations can be adapted for use. The container can provide a sealed environment for containing the composition, and separation from the atmosphere. The container can prevent during storage undesirable degradation, e.g., from absorption of light and/or moisture from the atmosphere or surrounding environment. Provided are ready-to-use topical preparations of ascorbic acid in a multi-use container which is pre-filled with a storage stable topical composition (e.g., as described herein).

Additional packaging for the container can be included. In some cases, the packaging provides a further barrier that prevents absorption of light and/or moisture from the atmosphere or surrounding environment.

Methods of Preparation

Also provided by this disclosure are processes for stabilizing ascorbic acid for storage that include preparation of any one of the subject formulations (e.g., as described herein), e.g., by dissolving ascorbic acid in a non-aqueous solvent with a urea agent and one or more optionally additional components to provide a stable liquid composition capable of storage stability.

In some embodiments, the process includes combining:
1. 1% to 20% by weight urea agent selected from urea, hydroxyethyl urea, and combination thereof;
2. 10% to 94% by weight of a non-aqueous skin-compatible solvent comprising $C_{(3-6)}$polyol, ethoxydiglycol, dimethyl ether, or a combination thereof;
3. 5% or less (e.g. 0.1 to 5%) by weight of a cinnamic acid or derivatives there; and
4. optionally one or more additional agents; with
5. 5% to 28% by weight ascorbic acid;

thereby dissolving the ascorbic acid to produce storage stable, nonaqueous, single-phase clear liquid composition of ascorbic acid. In certain embodiments, the one or more additional agents are combined and include: 0.5% to 2% *Pinus pinaster* bark extract. In certain embodiments, the one or more additional agents are combined and include: 3% to 10% by weight azelaic acid.

In some embodiments, the process further includes: combining 0.5% to 2% by weight of Vitamin E and 1.5% to 5% by weight of an emulsifying agent to produce a second liquid composition; and combining the second liquid composition with the liquid composition of ascorbic acid to produce an emulsion. In some embodiments, the process further includes: combining 0.5% to 2% by weight of a lipid component and 1.5% to 5% by weight of an emulsifying agent to produce a second liquid composition; and combining the second liquid composition with the liquid composition of ascorbic acid to produce an emulsion.

In some embodiments of the process, the one or more additional agents are combined and include: 0.5% to 2% by weight hydroxy acid. In certain embodiments, the hydroxy acid is selected from glycolic acid, lactic acid, mandelic acid, salicylic acid, capryloyl salicylic acid, salicyloyl phytosphingosine, gluconolactone, lactobionic acid, maltobionic acid, and combinations thereof.

Also provided are product storage stable formulations produced by the process according to any one of the embodiments described herein.

Definitions

The following definitions are set forth to illustrate and define the meaning and scope of the terms used in the description.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

"At least one" means one or more, and also includes individual components as well as mixtures/combinations.

Numbers used in describing quantities of ingredients and/or reaction conditions are to be understood as being modified in all instances by the term "about." Unless otherwise indicated, percentages and ratios are to be understood as based upon the total weight of the concentrate.

Numerical ranges are meant to include numbers within the recited range, and combinations of subranges between the given ranges. For example, a range from 1-5 includes 1, 2, 3, 4 and 5, as well as subranges such as 2-5, 3-5, 2-3, 2-4, 1-4, etc.

The terms "formulation" and "composition" are used interchangeably herein.

The term "non-aqueous" refers to compositions that are substantially anhydrous. Non-limiting examples of substantially anhydrous compositions include, for example, 1% by weight or less water in the subject compositions, such as 0.5% or less, 0.4% or less, 0.3% or less, 0.2% or less, or 0.1% or less by weight water.

It is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are described herein.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed. All patents and publications referred to herein are expressly incorporated by reference.

ADDITIONAL EMBODIMENTS

Additional Embodiments of this disclosure are described in the following aspects.

Aspect 1. A storage stable topical composition comprising:
5% to 28% by weight ascorbic acid;
5% to 20% by weight of a urea agent;
0.1% to 5% by weight of a cinnamic acid or derivative thereof; and
less than 10% by weight in total of one or more optional additional components;
dissolved in a non-aqueous skin-compatible solvent comprising polyol, C(2-6) alkanediol, glycol ether, dimethyl ether, or a combination thereof wherein the ascorbic acid is dissolved at a concentration (AA) that is above its maximum concentration in the solvent alone (X), and the urea is dissolved at a concentration that is at least (AA–X)*1.25.

Aspect 2. The composition of aspect 1, wherein the composition demonstrates less than 10 mol % degradation of the ascorbic acid after storage for 6 weeks at 40° C.±2° C. in a sealed container.

Aspect 3. The composition of aspect 1, wherein the composition demonstrates less than 5 mol % degradation of the ascorbic acid after storage for 8 months at 40° C.±2° C. in a multi-use container.

Aspect 4. The composition of aspect 1, wherein the composition demonstrates less than 10 mol % degradation of the ascorbic acid after storage for 16 months at 40° C.±2° C. in a multi-use container.

Aspect 5. The composition of any one of aspects 1-4, wherein the urea agent is urea.

Aspect 6. The composition of any one of aspects 1-4, wherein the urea agent is hydroxyethyl urea.

Aspect 7. The composition of any one of aspects 1-4, wherein the urea agent comprises a mixture of urea and hydroxyethyl urea.

Aspect 8. The composition of any one of aspects 1-7, wherein the solvent is selected from 1,3 propanediol, 1,2 propanediol, 1,3 butanediol, 1,5 pentanediol, 1,2 hexanediol, 1,6 hexanediol, 1,2 hexanediol, glycerol, diglycerol, ethoxydiglycol, dimethyl isosorbide, and a combination thereof.

Aspect 9. The composition of aspect 8, wherein the solvent is 1,3 propanediol.

Aspect 10. The composition of aspect 8, wherein the solvent is a mixture of 1,3 propanediol and 1,2 hexanediol.

Aspect 11. The composition of any one of aspects 1-10, wherein the one or more optional additional components are selected from tocopherols, tocotrienols (e.g., alpha, beta, delta and gamma tocopherols or alpha, beta, delta and gamma tocotrienols), azelaic acid, hydroxy acids (e.g., salicylic acid), panthenol, *Pinus pinaster* bark extract, emulsifying agent, hyaluronic acid complex, madecassoside, acetyl zingerone, bakuchiol, and bis-ethylhexylhydroxydimethoxybenzylmalonate.

Aspect 12. The composition of any one of aspects 1-11, wherein the composition comprises about 5% by weight of ascorbic acid.

Aspect 13. The composition of any one of aspects 1-11, wherein the composition comprises about 10% to about 20% by weight of ascorbic acid.

Aspect 14. The composition of aspect 13, wherein the composition comprises about 10% by weight of ascorbic acid.

Aspect 15. The composition of aspect 13, wherein the composition comprises about 15% by weight of ascorbic acid.

Aspect 16. The composition of aspect 13, wherein the composition comprises about 20% by weight of ascorbic acid.

Aspect 17. The composition of any one of aspects 1-11, wherein the composition comprises about 25% by weight of ascorbic acid.

Aspect 18. The composition of any one of aspects 13-16, wherein the ratio of ascorbic acid to urea agent is 1.8 to 2.2.

Aspect 19. The composition of aspect 18, wherein the ratio of ascorbic acid to urea agent is 2 to 1.

Aspect 20. The composition of any one of aspects 18-19, wherein the optional additional component comprises acetyl zingerone.

Aspect 21. The composition of aspect 20, wherein the composition comprises 2% or less by weight of the acetyl zingerone.

Aspect 22. Aspect The composition of aspect 21, wherein the composition comprises about 0.5% by weight of the acetyl zingerone.

Aspect 23. The composition of any one of aspects 1-19, wherein the cinnamic acid derivative is selected from ferulic acid, caffeic acid, coumaric acid, sinapinic acid, and derivatives thereof.

Aspect 24. The composition of any one of aspects 15 and 18-23, wherein the composition comprises:
about 15% by weight ascorbic acid;
about 8% by weight urea agent;
about 1% by weight ferulic acid; and
a solvent that comprises 1,3-propanediol.

Aspect 25. The composition of aspect 23, wherein the composition comprises 0.1 to 2% by weight of the ferulic acid.

Aspect 26. The composition of aspect 23, wherein the composition comprises 1% or less by weight of the ferulic acid.

Aspect 27. The composition of aspect 26, wherein the composition comprises about 0.5% by weight of the ferulic acid.

Aspect 28. The composition of aspect 1, wherein the composition comprises 60% by weight of the solvent comprising propanediol.

Aspect 29. The composition of aspect 1, wherein the composition comprises 10% by weight urea.

Aspect 30. The composition of aspect 1, wherein the composition comprises 0.5% by weight of diglycerin and *Pinus pinaster* bark extract.

Aspect 31. The composition of any one of aspects 16 and 23, wherein the composition comprises:
20% by weight ascorbic acid;
10% by weight urea agent
0.5% by weight ferulic acid;
60% by weight propanediol; and
0.5% by weight diglycerin and *Pinus pinaster* bark extract.

Aspect 32. The composition of any one of aspects 16 and 23, wherein the composition comprises:
20% by weight ascorbic acid;
10% by weight urea agent
0.5% by weight ferulic acid; and
a solvent that is 1,3-propanediol.

Aspect 33. The composition of any one of aspects 15 and 23, wherein the composition comprises:
15% by weight ascorbic acid;
8% by weight urea agent;
0.5% by weight ferulic acid; and
a solvent that is 1,3-propanediol.

Aspect 34. The composition of any one of aspects 13-14, wherein the ratio of ascorbic acid to urea agent is between 3 and 3.5.

Aspect 35. The composition of any one of aspects 1-29, wherein the optional additional component comprises azelaic acid.

Aspect 36. The composition of aspect 31, wherein the composition comprises 3% to 10% by weight of the azelaic acid.

Aspect 37. The composition of aspect 31, wherein the composition comprises about 7.5% by weight of the azelaic acid.

Aspect 38. The composition of any one of aspects 14, 23, and 31, wherein the composition comprises:
about 10% by weight ascorbic acid;
about 3% by weight urea agent;
about 0.5% to 2% by weight ferulic acid; and
a solvent that is 1,3-propanediol.

Aspect 39. The composition of any one of aspects 1-38, wherein the one or more optional additional components comprises *Pinus pinaster* bark extract.

Aspect 40. The composition of aspect 39, wherein the composition comprises 2% or less by weight of the *Pinus pinaster* bark extract.

Aspect 41. The composition of aspect 39, wherein the composition comprises about 0.5% by weight of the *Pinus pinaster* bark extract.

Aspect 42. The composition of any one of aspects 1-41, wherein the one or more optional additional components comprises madecassoside (e.g., madecassoside asiaticoside).

Aspect 43. The composition of any one of aspects 1-13, wherein the ratio of ascorbic acid to urea agent is a ratio from 1.0 to 1.3.

Aspect 44. The composition of any one of aspects 1-13, wherein the ratio of ascorbic acid to urea agent is 1.25 to 1.

Aspect 45. The composition of any one of aspects 1-44, wherein the optional additional component comprises a hydroxy acid.

Aspect 46. The composition of aspect 45, wherein the hydroxy acid is selected from glycolic acid, lactic acid, mandelic acid, salicylic acid, capryloyl salicylic acid, salicyloyl phytosphingosine, gluconolactone, lactobionic acid, maltobionic acid, and combinations thereof.

Aspect 47. The composition of aspect 45, wherein the hydroxy acid is salicylic acid.

Aspect 48. The composition of aspect 45, wherein the composition comprises 3% or less by weight of the hydroxy acid.

Aspect 49. The composition of aspect 45, wherein the composition comprises about 2% by weight of the hydroxy acid.

Aspect 50. The composition of aspect 17, wherein the composition comprises:
about 25% by weight ascorbic acid;
about 20% by weight urea agent;
about 0.5% to 2% by weight ferulic acid; and
a solvent that is 1,3-propanediol.

Aspect 51. The composition of aspect 1, wherein the ratio of ascorbic acid to urea agent is 1 to 1.

Aspect 52. The composition of any one of aspects 1-23, wherein the optional additional component comprises panthenol.

Aspect 53. The composition of aspect 52, wherein the composition comprises 10% or less by weight of the panthenol.

Aspect 54. The composition of aspect 52, wherein the composition comprises about 5% by weight of the panthenol.

Aspect 55. The composition of any one of aspects 12 and 51, wherein the composition comprises:
about 5% by weight ascorbic acid;
about 5% by weight urea agent; and
about 0.1 to 2% by weight of ferulic acid;
a solvent that is 1,3-propanediol.

Aspect 56. The composition of any one of aspects 51-54, wherein the one or more optional additional components comprises madecassoside (e.g., madecassoside asiaticoside).

Aspect 57. The composition of aspect 42, wherein the composition comprises about 1% or less by weight of the madecassoside.

Aspect 58. An emulsion composition, comprising:
the composition according to any one of aspects 1-57;
an oil component; and
an optional emulsifying agent.

Aspect 59. The emulsion composition of aspect 58, wherein the oil component is silicone-based.

Aspect 60. The emulsion composition of aspect 58 or 59, wherein the emulsion composition comprises an emulsifying agent.

Aspect 61. The emulsion composition of any one of aspects 58-59, wherein the emulsifying agent is selected from polysorbates, laureth-4, potassium cetyl sulfate and silicone and silicone-elastomer-based emulsifiers and emulsifying blends.

Aspect 62. A ready-to-use topical preparation of ascorbic acid in a multi-use container which is pre-filled with a storage stable topical composition according to any one of aspects 1-57, wherein the multi-use container comprises means for dispensing a single dose of the storage stable topical composition.

Aspect 63. The preparation of aspect 62, wherein the storage stable topical composition demonstrates less than 10 mol % degradation of the ascorbic acid after storage for 6 weeks at 40° C.±2° C. in the container.

Aspect 64. The preparation of aspect 62, wherein the storage stable topical composition demonstrates less than 10 mol % degradation of the ascorbic acid after storage for 6 months at 25° C.±2° C. in the container.

Aspect 65. The preparation of any one of aspects 58-60, wherein the storage stable topical composition is sealed in the container.

Aspect 66. The preparation of any one of aspects 58-61, wherein the container is placed in packaging.

Aspect 67. A process for stabilizing ascorbic acid for storage, the process comprising:
combining:
1% to 20% by weight urea agent selected from urea, hydroxyethyl urea, and combination thereof;
10% to 94% by weight of a non-aqueous skin-compatible solvent comprising C(3-6)polyol, ethoxydiglycol, dimethyl ether, or a combination thereof;
0.1 to 5% or less of a cinnamic acid or derivatives thereof and
optionally one or more additional agents; with
5% to 28% by weight ascorbic acid;
thereby dissolving the ascorbic acid to produce storage stable, nonaqueous, single-phase clear liquid composition of ascorbic acid.

Aspect 68. The process of aspect 67, wherein the one or more additional agents are combined and comprise:
0.5% to 2% *Pinus pinaster* bark extract.

Aspect 69. The process of aspect 67, wherein the one or more additional agents are combined and comprise:
3% to 10% by weight azelaic acid.

Aspect 70. The process of aspect 67, further comprising:
combining 0.5% to 2% by weight of acetyl zingerone and 1.5% to 5% by weight of an emulsifying agent to produce a second liquid composition; and
combining the second liquid composition with the liquid composition of ascorbic acid to produce an emulsion.

Aspect 71. The process of aspect 67, further comprising:
combining 0.5% to 2% by weight of a lipid component and 1.5% to 5% by weight of an emulsifying agent to produce a second liquid composition; and
combining the second liquid composition with the liquid composition of ascorbic acid to produce an emulsion.

Aspect 72. The process of aspect 71, wherein the lipid component is selected from cholesterol, ceramides, free fatty acids, and combinations thereof.

Aspect 73. The process of aspect 67, wherein the one or more additional agents are combined and comprise:
0.5% to 2% by weight hydroxy acid.

Aspect 74. The process of aspect 73, wherein the hydroxy acid is selected from glycolic acid, lactic acid, mandelic acid, salicylic acid, capryloyl salicylic acid, salicyloyl phytosphingosine, gluconolactone, lactobionic acid, maltobionic acid, and combinations thereof.

Aspect 75. A product produced by the process according to any one of aspects 67-74.

Aspect 76. The product of aspect 75, wherein the product is used for wound healing Aspect 77. The product of aspect 75, wherein the product is a serum.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The invention is further defined by reference to the following examples. These examples are representative, and should not be construed to limit the scope of the invention.

EXAMPLES

Example 1: Assessment of Formulation Components

A series of experiments were performed to assess and optimize the components of the subject formulations. AA refers to L-ascorbic acid. U refers to urea. % values are wt %.

Summary of Experiments

Ascorbic Acid to Urea
- The maximum amount of AA solubilized in 1,3-propanediol before recrystallization was ~12%. This solubility limit was also observed for propylene glycol (1,2 propanediol).
- First: completely solubilized AA/U in 1,3 propanediol at 20% AA, and 15% U.
  - Reduced to 10% U content, and still no recrystallization.
  - Reduced to 5% U content, and recrystallization occurred.
  - Tested 8% U content and recrystallization occurred.
  - 10% U content thus appeared to be close to the minimum amount U required to solubilize 20% AA.
- U in combination with a 15% AA content:
  - 5% U prevented recrystallization
  - 3.75% U prevented recrystallization
  - 2.5% U resulted in recrystallization
- Maximum saturation level experiments
  - 30% AA, 20% U in 1,3 propanediol resulted in recrystallization
  - 28% AA, 20% U resulted in fully solubilized AA with no recrystallization
  - The limitation of this composition is the solubility of U in 1,3 propanediol-~27.8% saturation can be reached before recrystallization of U becomes apparent
- Using these numbers is how the following equation was obtained for determining the amount of U, and thus the ratio of AA to U in high concentration ascorbic acid formulations:
  - $(AA-X)*1.25=U$ %, where X=the maximum % solubility of AA in the chosen solvent. In this case, X=12%, as noted above.

The equation is relevant to compositions including a lower limit of 5% ascorbic acid because the inclusion of other polyols that provide very low or virtually no solubility of AA, such as dimethyl isosorbide (DMI). Therefore, when a mixture of propanediol and DMI is used as the solvent, for example, the X value can be 5% (maximum solubility of AA), depending on the ratio of propanediol and DMI used.

Solvents 1,3 propanediol, 1,2 propanediol, butylene glycol, pentylene glycol, and hexanediol were identified as preferred solvents. 1,3 propanediol (trade name: Zemea) is inherently different from and preferable to the various polyols described. Below is a review of various polyols and reasons why 1,3 propanediol is unique and preferable:

1,3-propanediol, sometimes referred to in the art as propanediol, is unique in that it possesses a combination of gentleness on skin (even applied neat, or at 100% concentration), relatively low viscosity (and therefore perceived "lightness" on skin), environmental friendliness (not petroleum-derived), natural derivation (corn or sugar cane), low odor, and moderate ability to solubilize ascorbic acid.

1,2-propanediol, otherwise referred to in the art as propylene glycol, although of low viscosity and possessing a moderate ability to solubilize ascorbic acid, is well-known for inducing skin irritation and sensitivity. Additionally, it is derived from petroleum and possesses an unpleasant odor, reminiscent of acetone.

1,3-butanediol, otherwise referred to in the art as butylene glycol, is of low viscosity, possesses a moderate ability to solubilize ascorbic acid, and is relatively gentle on skin. However, like propylene glycol, it is derived from petroleum (not environmentally friendly) and possesses an unpleasant odor, reminiscent of acetone.

also applicable to dipropylene glycol 1,5-pentanediol, otherwise referred to in the art as pentylene glycol, possesses a moderate ability to solubilize ascorbic acid, low odor, and certain versions are not derived from petroleum but from sugarcane or corn. However, upon application to skin, it imparts a "heavier", less desirable texture on skin. Additionally, its recommended use level is capped at 5%, limiting usage as a primary solvent.

1,2-hexanediol possesses a moderate ability to solubilize ascorbic acid. However, upon application to skin, it imparts a "heavier", less desirable texture on skin, possesses an unpleasant odor reminiscent of acetone, and is derived from petroleum. Additionally, its recommended use level is capped at 10%, limiting usage as a primary solvent.

Glycerin and diglycerin, possess a moderate ability to solubilize ascorbic acid, are relatively gentle on skin, are low-odor, and are not derived from petroleum. However, they are of a very viscous nature, and impart not only an undesirable, "heavy" texture on skin, but one that is exceedingly sticky.

Dimethyl isosorbide is relatively gentle on skin and not derived from petroleum, and imparts a "light", not undesirable texture when applied to skin. However, it has a very limited ability to solubilize ascorbic acid and possesses a slight, but noticeable chemical odor reminiscent of chlorine.

Urea Agents

Urea is preferable to hydroxyethyl urea. There are a number of reasons for this:
- Urea, when used in sufficient low concentrations (10-15% and below) in leave-on applications, possesses desirable humectant, barrier-repairing and very mild keratolytic properties, which in combination are very effective at improving the feel and look of dry and/or rough skin.
- Urea is naturally present not only in the human body but specifically in the skin, where it acts as a natural moisturizing factor (NMF).
- Hydroxyethyl urea possesses similar humectant properties, but not the same level of barrier-repairing and mild keratolytic properties of urea.
- Additionally, hydroxyethyl urea may contain trace amounts of diethanolamine, which is listed as a potential carcinogen by California's Proposition 65, and requires a warning on products sold to consumers. For this reason, at least one manufacturer of hydroxyethyl urea has stated that it will discontinue production of this ingredient (AkzoNobel).

Optional Additional Components

Additional ingredients were chosen for their compatibility with (e.g., miscibility in) 1,3 propanediol, 1,2 propanediol, and 1,3 butanediol. Additional notes and observations on each optional additional component are shown below.

Panthenol (Pro-Vitamin B5)

This is a humectant that shows soothing and moisturizing properties for skin. Both enantiomers, D-panthenol and L-panthenol, are potent humectants. However, only D-panthenol is converted into pantothenic acid in the skin, which confers additional benefits to skin (wound healing, for example).

Research shows that it can reduce irritation to skin by other ingredients

Research also shows barrier-repairing ability (stimulation of physiologic lipid synthesis)

DL-panthenol is a racemic mixture of the two enantiomers; it is in powdered/crystal form.

D-panthenol is a viscous liquid.

DL-panthenol is freely soluble in 1,3 propanediol, 1,2 propanediol and 1,3 propanediol (up to 50%)

D-panthenol is also freely soluble in 1,3 propanediol, 1,2 propanediol and 1,3 propanediol, with no risk of recrystallization at any concentration (as it is already liquid at room temperature).

Inhibition of transepidermal water loss is apparent at concentrations of 1% and above.

Hyaluronic Acid

Hyaluronic acid is a humectant that shows the ability to form a viscoelastic film on skin that prevents transepidermal water loss.

It is usually incorporated in aqueous solutions in its salt form, sodium hyaluronate However, there is a raw material blend that is largely free from water, in which it is incorporated in a vehicle of glyceryl polymethacrylate, butylene glycol (1,3 butanediol), and natto gum (trade name Hydrafilm 3MW by The Innovation Company). This makes it compatible with the non-aqueous formulations of the present disclosure.

Documents from The Innovation Company show usage of this material up to 9.1% by weight of the final formula.

The chemical composition is as follows:

75-85% glyceryl polymethacrylate 15-20% butylene glycol 0.5-2% natto gum 0.5-2% hyaluronic acid.

*Pinus Pinaster* Bark Extract

Components of the bark extract of *Pinus pinaster* species show the ability to recycle vitamin C.

Additionally, there is research to show their general antioxidant, anti-inflammatory and anti-acne properties.

pycnogenol may be used as an alternative when *Pinus pinaster* bark extract is desired, a material blend from Kinetik called Pantrofina Skin360 (PS360) is utilized in the subject formulations PS360, unlike pycnogenol, is already in liquid form as it uses diglycerin as a solvent, making it very easy to incorporate Additionally, Res Pharma Industriale provides in-vitro and clinical data to show effectiveness against free radical damage, inflammation and acne at a concentration of 0.5% by weight of PS360

The chemical composition is as follows:

90-95% diglycerin 5-10% *Pinus pinaster* bark extract

Madecassoside

Centella *Asiatica* extract is often used for its soothing properties.

Madecassoside is a highly purified glycosylated triterpene of Centella *Asiatica*. It is sold by raw material supplier SEPPIC, who share in-vitro and clinical data showing its anti-inflammatory and other effects on skin.

This is a very expensive ingredient ($6.10 per gram), but clinical data from SEPPIC shows desirable ability to reduce erythema (skin redness) in concentrations of 0.2%.

At a concentration of 0.2%, madecassoside is soluble in 1,3 propanediol, 1,2 propanediol and 1,3 butanediol.

In some embodiments, the madecassoside is madecassoside asiaticoside.

Azelaic Acid

Azelaic acid (AzA) is well studied for its ability to treat acne, rosacea and melasma, due to the fact that it was studied and sold as a prescription drug. Though poorly understood, these effects are believed to be a result of AzA's anti-bacterial, anti-inflammatory, and keratolytic effects, as well as its unique ability to cause apoptosis in abnormal melanocytes.

It is very poorly soluble in most solvents. As a result, all products currently on the market, both prescription and cosmetic, are sold as opaque emulsions, where the AzA is not solubilized but instead finely milled into a powder and suspended in the viscous vehicle.

Because of an inability to solubilize AzA, a preferred component for maximizing delivery into the skin of active ingredients, the team behind prescription product Finacea (currently considered to be the gold standard) chose to manipulate pH, as they discovered that, counterintuitively, a salt form of AzA (formed in aqueous environments in which the pH is higher than the pKa of AzA, 4.15), is slightly better at penetrating skin.

I've discovered that AzA can be solubilized in 1,3 propanediol at relatively high concentrations—up to 10%.

The solubility of AzA in 1,3 propanediol can be slightly increased by the presence of hydroxyethyl urea.

For example, it is possible to solubilize 7.5% AzA with 10% AA, 5% U in a 1,3 propanediol base.

Ferulic Acid

Ferulic acid is an antioxidant that increases AA's photoprotective effect on skin. It can also somewhat stabilize AA in aqueous systems.

Ferulic acid is readily soluble in 1,3 propanediol, 1,2 propanediol, 1,3 butanediol and dimethyl isosorbide isosorbide can increase the effectiveness of ferulic acid by enhancing skin penetration.

Stabilizes AA and provides antioxidant activity and photoprotection.

Acetyl Zingerone

Acetyl zingerone is a broad-spectrum antioxidant that can prevent lipid peroxidation. It was engineered to be a more stable, more potent derivative of zingerone.

Sytheon provides in-vitro and clinical data showing its antioxidant, photoprotective, and anti-aging properties Acetyl zingerone may be used as a replacement for tocopherol.

Acetyl zingerone is readily soluble in 1,3 propanediol, 1,2 propanediol and 1,3 butanediol at the desired concentrations (0.5-1%), eliminating the need for emulsifiers as would be required for tocopherol Glycyrrhizic Acid Glycyrrhizic acid, like many other derivatives from licorice root (*Glycyrrhiza Glabra, Glycyrrhiza Uralensis*), shows anti-inflammatory, antioxidant and skin lightening properties.

Unlike 18B-glycyrrhetinic acid, glycyrrhizic acid shows solubility in 1,3-propanediol.

other derivatives of licorice root can be use, such as dipotassium glycyrrhizate, monoammonium glycyrrhizate, etc.

Example 2: Exemplary Formulations

The exemplary formulations of Table 2 were prepared and assessed.

TABLE 2

Exemplary Formulations 1-3

| Formulation | 1,3-propanediol | urea | L-ascorbic acid | ferulic acid |
|---|---|---|---|---|
| 1 (Serum) | 69.5% | 10% | 20% | 0.5% |
| 2 (Rinse-Off Mask) | 51.5% | 20% | 28% | 0.5% |
| 3 (Serum) | 79% | 5% | 15% | 1% |

Example 4: Exemplary Formulations

Ratio of Ascorbic Acid to Urea

In order to determine a desirable ratio of ascorbic acid to urea for the compositions of this disclosure, the maximum concentration for ascorbic acid that can be solubilized is first determined, with heat exposure (not exceeding 80° C. in order to prevent degradation of ascorbic acid), in a given solvent without precipitation upon cooling. Experiments revealed this concentration to be approximately 10-12% for 1,3 propanediol, propylene glycol (1,2 propanediol) and butylene glycol (1,3 butanediol), and significantly lower for dimethyl isosorbide.

Next, concentrations of ascorbic acid beyond the aforementioned maximum concentration are solubilized, using urea as a co-solvent. Repeated experiments of this nature, using differing concentrations and ratios of urea to ascorbic acid, revealed the following relationship between these two substances (ascorbic acid and urea) that is useful to create fully solubilized composition which is storage stable:

$$(AA-X)*1.25=U$$

AA=concentration of ascorbic acid
X=maximum solubilization point of ascorbic acid in solvent of choice
U=concentration of urea Compositions having an ascorbic acid concentration as low as 5% can be prepared in cases where the polyol solvents used provide very low solubility, such as dimethyl isosorbide (DMI). Therefore, a mixture of propanediol and DMI, for example, can yield an X value of 5% (maximum solubility of AA), depending on the ratio of propanediol and DMI.

In general, 1,3 propanediol is preferred over 1,2 propanediol, butylene glycol, pentylene glycol, or hexanediol. 1,3 propanediol is preferable to various polyols described in the art. Below is a review of various polyols and reasons why 1,3 propanediol is unique and preferable:

1,3 propanediol, otherwise referred to in the art as propanediol, is unique in that it possesses a combination of gentleness on skin (even applied neat, or at 100% concentration), relatively low viscosity (and therefore perceived "lightness" on skin), environmental friendliness (not petroleum-derived), natural derivation (corn or sugar cane), low odor, and moderate ability to solubilize ascorbic acid.

1,2 propanediol, otherwise referred to in the art as propylene glycol, although of low viscosity and possessing a moderate ability to solubilize ascorbic acid, induces skin irritation and sensitivity. Additionally, it is derived from petroleum and possesses an unpleasant odor, reminiscent of acetone.

1,3 butanediol, otherwise referred to in the art as butylene glycol, is of low viscosity, possesses a moderate ability to solubilize ascorbic acid, and is relatively gentle on skin. However, like propylene glycol, it is derived from petroleum (not environmentally friendly) and possesses an unpleasant odor, reminiscent of acetone.

Note that these properties also apply to dipropylene glycol.

1,5 pentanediol, otherwise referred to in the art as pentylene glycol, possesses a moderate ability to solubilize ascorbic acid, low odor, and certain versions are not derived from petroleum but from sugarcane or corn. However, upon application to skin, it imparts a "heavier", less desirable texture on skin. Additionally, its recommended use level is generally capped at 5%, limiting usage as a primary solvent.

1,2 hexanediol possesses a moderate ability to solubilize ascorbic acid. However, upon application to skin, it imparts a "heavier", less desirable texture on skin, possesses an unpleasant odor of acetone, and is derived from petroleum. Additionally, its recommended use level is capped at 10%, limiting usage as a primary solvent.

Glycerin and diglycerin, possess a moderate ability to solubilize ascorbic acid, are relatively gentle on skin, are low-odor, and are not derived from petroleum. However, they are highly viscous, and impart not only an undesirable "heavy" texture on skin, but one that is exceedingly sticky.

Dimethyl isosorbide is relatively gentle on skin and not derived from petroleum, and imparts a "light", not undesirable texture when applied to skin. However, it has a very limited ability to solubilize ascorbic acid and possesses a slight, but noticeable chemical odor reminiscent of chlorine.

Urea is preferable to hydroxyethyl urea. There are a number of reasons for this, as summarized below:

Urea, when used in sufficient low concentrations (10-15% and below) in leave-on applications, possesses desirable humectant, barrier-repairing and very mild keratolytic properties, which in combination are very effective at improving the feel and look of dry and/or rough skin. Urea is naturally present not only in the human body but specifically in the skin, where it acts as a natural moisturizing factor (NMF).

Hydroxyethyl urea possesses similar humectant properties, but not the barrier-repairing and mild keratolytic properties of urea. Additionally, hydroxyethyl urea may contain trace amounts of diethanolamine, a potential carcinogen.

Additional ingredients can be included which are compatible with the ascorbic acid/solvent/urea combination of interest.

The exemplary formulations of Table 3 were prepared and assessed as having desirable properties including storage stability.

TABLE 3

Components of Exemplary Compositions (% by weight)

| Formulation | 1 | 2 | 3 | 4 | 5 | 6 | 7 | 8 |
|---|---|---|---|---|---|---|---|---|
| ascorbic acid | 5% | 5% | 10% | 15% | 15% | 20% | 25% | 20% |
| urea/hydroxyethyl urea | 5% | 5% | 3% | 8% | 10% | 10% | 20% | 10% |

TABLE 3-continued

Components of Exemplary Compositions (% by weight)

| Formulation | 1 | 2 | 3 | 4 | 5 | 6 | 7 | 8 |
|---|---|---|---|---|---|---|---|---|
| Ferulic acid | 0.5% | 0.5% | 0.5% | 1% | 0.5% | 0.5% |  | 0.5% |
| C3-C6 polyol | 83.8% 1,3-propanediol | 53.3% 1,3-propanediol | 75.3% 1,3-propanediol | 72.9% 1,3-propanediol | 48% 1,3 propanediol | 69% 1,3-propanediol | 53% 1,3 propanediol | 60% 1,3 propanediol |
| Additive 1 | 5% panthenol | 5% panthenol | 7.5% azelaic acid | .5% acetyl zingerone (trade name Synoxyl AZ) | 1% tocopherol | 0.5% pinus pinaster extract (diglycerin, pinus pinaster bark extract; trade name Pantrofina Skin360) | 2% salicylic acid |  |
| Additive 2 | 0.2% madecassoside | 0.2% madecassoside | 0.5% pinus pinaster extract (diglycerin, pinus pinaster bark extract; trade name Pantrofina Skin360) | 0.5% pinus pinaster extract (diglycerin, pinus pinaster bark extract; trade name Pantrofina Skin360) | .5% Bis-Ethylhexyl Hydroxy-dimethoxy Benzylmalonate (trade name Ronacare AP) |  |  | 0.5% diglycerin, Pinus Pinaster Bark Extract |
| Additive 3 | 0.5% pinus pinaster extract (diglycerin, pinus pinaster bark extract; trade name Pantrofina Skin360 | 0.5% pinus pinaster extract (diglycerin, pinus pinaster bark extract; trade name Pantrofina Skin360) | 0.2% madecassoside | 5% panthenol | 5% silicone-based emulsifier (dimethicone, dimethicone/peg-10/15 crosspolymer; trade name KSG-280) |  |  |  |
| Additive 4 |  | 15% dimethyl isosorbide | 3% panthenol | 0.1% madecassoside | 5% silicone-based emulsifier (Lauryl PEG-9 Polydimethyl-siloxyethyl Dimethicone) |  |  |  |
| Additive 5 |  | 30% silicone-based emulsifier (dimethicone, dimethicone/peg-10/15 crosspolymer; trade name KSG-280) |  |  | 15% isododecane |  |  |  |
| Additive 6 |  | .5% Bis-Ethylhexyl Hydroxy-dimethoxy Benzylmalonate (trade name Ronacare AP) |  |  |  |  |  |  |

Other variations: dimethyl isosorbide, caprylyl glycol or decylene glycol can be utilized as an alternative or additional solvents in the compositions of Table 2 or Table 3.

Example 3: Storage Stability Studies

Stability Method

Samples are stored in sealed containers, sealed from the atmosphere, at 40 degrees Celsius for up to 12 weeks. Results at 0 to 8 weeks are shown in Table 4. In general, 8 weeks storage under these conditions is expected to be equivalent to storage for 16 months at room temperature. The compositions in the containers are sampled at each time point, and assessed for levels of degradation of vitamin C using HPLC analysis.

Compositions

Exemplary compositions were prepared containing either approx. 20% vitamin C (Formulation 6 referred to in Table 3)

The storage stability of these compositions was compared to control compositions that included clinically comparable amount of vitamin C (15%) dissolved in water with the addition of a ferulic acid in a concentration of 0.5%, tocopherol in a concentration of 1%, with additional components of a glycol ether, alkanediol, laureth-23, panthenol, triethanolamine, phenoxyethanol, and sodium hyaluronate. The results are shown in Table 4. The exemplary serum (approx. 15% vitamin C) compositions are still within specification after weeks 8 of testing (or the equivalent to 16 months at room temperature), as opposed to the control compositions which fell out of specification (OOS) by week 2 of testing (or equivalent to 4 months at room temperature).

TABLE 4

Storage stability

| Storage time | | % vitamin C by HPLC | |
|---|---|---|---|
| Week 40° C. | Equiv. Months RT | Serum | Serum Control |
| 0 | 0 | 100.35% | 99.20% |
| 1 | 2 | 99.80% | 91.60% |
| 2 | 4 | 97.30% | *85.87% |
| 4 | 8 | 95.45% | *81.73% |
| 8 | 16 | 94.25% | *79.27% |

*indicates the samples were assessed as being OOS according to Out of Specification (OOS) Standards: 90% or less vitamin C stability.

Example 4: Comparative Studies

U.S. Pat. No. 6,020,367 (patent '367) attempted to show the viability of "supersaturated solutions" of vitamin C in a polyol. Several compositions of patent '367 were prepared in accordance with the disclosure, However, many of the "supersaturated solutions" of vitamin C patent '367 do not actually remain solubilized at room temperature over time. Rather, the solutions lead to development of vitamin C crystals which at first create a cloudy appearance and then settle downward. Such compositions are non-uniform and unsuitable for use as end products.

Glycerin Solvent

A mixture of 25% ascorbic acid and 75% glycerin was prepared. The ascorbic acid was and solubilized with heating at 95° C. to produce a transparent solution. Upon cooling to room temperature, crystallization became apparent within the first 24 hours of storage.

Butylene Glycol Solvent

According to patent '367 butylene glycol has a lower ability to solubilize ascorbic acid. A mixture of 25% ascorbic acid and 75% butylene glycol was prepared. Even with heating at the maximum temperature of 95° C. (under agitation), butylene glycol failed to solubilize the ascorbic acid content, leaving a "cloudy" appearance and sedimentation upon cessation of agitation.

Propylene Glycol Solvent

According to patent '367 propylene glycol has the lowest ability of these solvents to solubilize ascorbic acid. A mixture of 25% ascorbic acid and 75% propylene glycol was prepared. The ascorbic acid was and solubilized with heating at 95° C. to produce a transparent solution. Upon cooling to room temperature, crystallization became apparent within the first 24 hours of storage.

It is important to note the fragile nature of ascorbic acid renders it sensitive not only to the presence of water and air, but also heat. When heated above 80° C., even in anhydrous vehicles such as polyols, there is a risk for degradation of the ascorbic acid. The solutions described above prepared according to the direction of patent '367, when heated to the described range of 85-95° C., showed signs of degradation.

U.S. Publication No. 2007/0077261 (publication '261) discloses compositions including broad ranges of ascorbic acid and urea, but fails to identify both the "floor" (minimum amount of urea required to solubilize a certain amount of ascorbic acid) and the "ceiling" (maximum amount of ascorbic acid that can be solubilized through this method).

Example 3 of publication '261 discloses a composition including: 50% propylene glycol, 22% urea and 28% ascorbic acid, heated to 75° C. with agitation until transparent, then cooled to room temperature. This example was reproduced. The solution started to precipitate within 24 hours, demonstrating a failure to understand and elucidate the required ratio of urea to ascorbic acid.

Using the equation of this disclosure set forth above, the correct concentration of urea to solubilize 28% ascorbic acid in propylene glycol would be 20% (the proper "floor"). Indeed, a solution of 28% ascorbic acid and 20% urea in propylene glycol was prepared and remained fully solubilized even after 30 days of storage at room temperature. Furthermore, experiments reveal that these concentrations of ascorbic acid (28%) and urea (20%), also represent the maximum concentrations soluble in propylene glycol, butylene glycol and propanediol, before urea itself starts to precipitate in solution (the "ceiling").

Experiments showed that no concentration of urea within the 5-40% range can solubilize 40% ascorbic acid in a polyol base:
- 40% ascorbic acid, 5% urea, 55% propylene glycol
- 40% ascorbic acid, 10% urea, 50% propylene glycol
- 40% ascorbic acid, 20% urea, 40% propylene glycol
- 40% ascorbic acid, 40% urea, 20% propylene glycol All mixtures were heated to 85° C. However, none were solubilized even after agitation at maximum temperature of 85° C. In addition, the urea content disclosed in several examples of publication '261 is not only unnecessarily high (likely because of a failure to identify the "floor"), but also renders the compositions unusable as leave-on facial products and result in irritation of the skin such as burning and irritation, etc. These compositions, when applied to the face, produce an intense burning and stinging sensation that is immediately apparent. This is likely due to urea's keratolytic properties. Additionally, the urea content disclosed in several examples of publication '261 precipitated out of the formulation. In leave-on products intended for the face, maximum urea content is usually 10-15%. Higher concentrations of urea in leave on products than necessary can result of burning sensation of the skin.

Alternatively, formulation 5 of Table 3 and formulation 2 of Table 2 of the present disclosure is identified as a rinse-off product.

While the illustrative embodiments of the invention have been described with particularity, it will be understood that various other modifications will be apparent to, and can be readily made by those skilled in the art, without departing from the spirit and scope of the invention. Accordingly, it is not intended that the scope of the claims appended hereto be limited to the examples and descriptions set forth hereinabove but rather that the claims be construed as encompassing all the features of patentable novelty in the present invention, including all features which would be treated as equivalents by persons having ordinary skill in the art of formulating topically-applied personal care and dermatological products.

What is claimed is:

1. A storage stable topical composition comprising:
   a. 16% to 20% by weight ascorbic acid;
   b. 5 to 10% by weight of a solubility and penetrating agent that is a urea agent;
   c. 0.1% to 1% by weight of ferulic acid; and
   d. less than 10% by weight in total of one or more optional additional components;
   e. dissolved in a non-aqueous skin-compatible solvent comprising 1,3-propanediol; wherein the ascorbic acid is dissolved at a concentration (AA) that is above its maximum concentration in the solvent alone (X), and the urea agent is dissolved at a concentration that is (AA−X)*1.25;

wherein the composition is substantially free of water, and wherein the composition does not comprise niacinamide.

2. The composition of claim 1, wherein the composition demonstrates less than 10 mol % degradation of the ascorbic acid after storage for 6 weeks at 40° C.±2° C. in a sealed container.

3. The composition of claim 1, wherein the urea agent is urea, hydroxyethyl urea, or a mixture of urea and hydroxyethyl urea.

4. The composition of claim 1, wherein the solvent further comprises 1,2 propanediol, 1,3 butanediol, 1,5 pentanediol, 1,2 hexanediol, 1,6 hexanediol, 1,2 hexanediol, glycerol, diglycerol, ethoxydiglycol, dimethyl isosorbide, or any combination thereof.

5. The composition of claim 4, wherein the solvent further comprises 1,2 hexanediol.

6. The composition of claim 1, wherein the one or more optional additional components are selected from tocopherols, tocotrienols, azelaic acid, hydroxy acids, panthenol, *Pinus pinaster* bark extract, emulsifying agent, hyaluronic acid complex, madecassoside, acetyl zingerone, bakuchiol, and bis-ethylhexylhydroxydimethoxybenzylmalonate.

7. The composition of claim 6, wherein the composition comprises:
 20% by weight ascorbic acid;
 10% by weight urea agent;
 0.5% by weight ferulic acid;
 69% by weight 1,3-propanediol; and
 0.5% by weight in total of diglycerin and *Pinus pinaster* bark extract.

8. The composition of claim 6, wherein the composition comprises:
 20% by weight ascorbic acid;
 10% by weight urea agent; and
 0.5% by weight ferulic acid; and
 the solvent consists of 1,3-propanediol.

9. The composition of claim 6, wherein the composition consists of:
 20% by weight ascorbic acid;
 10% by weight urea agent;
 0.5% by weight ferulic acid;
 69% by weight 1,3-propanediol; and
 0.5% by weight in total of diglycerin and *Pinus pinaster* bark extract;
 wherein the composition is substantially free of water, and wherein the composition does not consist of niacinamide.

10. The composition of claim 1, wherein the composition comprises 20% by weight of ascorbic acid.

11. The composition of claim 1, wherein the ratio by weight of ascorbic acid to urea agent is 2 to 1.

12. The composition of claim 1, wherein the composition comprises at least 60% by weight of the solvent comprising 1,3-propanediol.

13. The composition of claim 1, wherein the composition comprises 10% by weight urea.

14. The composition of claim 1, wherein the composition comprises 0.5% by weight of diglycerin and *Pinus pinaster* bark extract.

15. The composition of claim 1, wherein the ratio by weight of ascorbic acid to urea agent is between 3 and 3.5.

16. The composition of claim 1, wherein the optional additional component comprises azelaic acid.

17. The composition of claim 16, wherein the composition comprises 3% to 10% by weight of the azelaic acid.

18. The composition of claim 1, wherein the one or more optional additional components comprises 2% or less by weight of *Pinus pinaster* bark extract.

19. The composition of claim 1, wherein the optional additional component is hydroxy acid is selected from glycolic acid, lactic acid, mandelic acid, salicylic acid, capryloyl salicylic acid, salicyloyl phytosphingosine, gluconolactone, lactobionic acid, maltobionic acid, and combinations thereof.

20. An emulsion composition, comprising:
 the composition of claim 1;
 an oil component; and
 an optional emulsifying agent.

21. The composition of claim 1, wherein the composition does not comprise vitamin E acetate.

22. The composition of claim 1, wherein the composition does not consist of niacinamide.

23. A storage stable topical composition comprising:
 20% by weight ascorbic acid;
 urea, wherein the ratio by weight of ascorbic acid to urea is 1.8 to 2.2;
 0.1% to 1% by weight of ferulic acid; and
 less than 1% by weight in total of *Pinus pinaster* bark extract;
 dissolved in a non-aqueous solvent comprising 60% to 75% by weight of 1,3-propanediol;
 wherein the composition is substantially free of water, and wherein the composition does not comprise niacinamide.

24. The composition of claim 23, wherein the composition consists essentially of:
 20% by weight ascorbic acid;
 10% by weight urea;
 0.5% by weight ferulic acid;
 less than 1% by weight in total of *Pinus pinaster* bark extract; and
 1,3-propanediol.

* * * * *